US012569240B2

(12) United States Patent
Kalhorn et al.

(10) Patent No.: US 12,569,240 B2
(45) Date of Patent: Mar. 10, 2026

(54) DECORTICATING SCREW

(71) Applicant: MUSC FOUNDATION FOR RESEARCH DEVELOPMENT, Charleston, SC (US)

(72) Inventors: Stephen Kalhorn, Mt Pleasant, SC (US); Mark Semler, Mt. Pleasant, SC (US); Christopher Hapstack, Charleston, SC (US); Joe Ruscito, Charleston, SC (US)

(73) Assignee: MUSC FOUNDATION FOR RESEARCH DEVELOPMENT, Charleston, SC (US)

( * ) Notice: Subject to any disclaimer, the term of this patent is extended or adjusted under 35 U.S.C. 154(b) by 752 days.

(21) Appl. No.: 17/639,038

(22) PCT Filed: Aug. 28, 2020

(86) PCT No.: PCT/US2020/048516
§ 371 (c)(1),
(2) Date: Feb. 28, 2022

(87) PCT Pub. No.: WO2021/041889
PCT Pub. Date: Mar. 4, 2021

(65) Prior Publication Data
US 2022/0304672 A1　Sep. 29, 2022

Related U.S. Application Data

(60) Provisional application No. 62/893,672, filed on Aug. 29, 2019.

(51) Int. Cl.
| | |
|---|---|
| *A61F 2/44* | (2006.01) |
| *A61B 17/04* | (2006.01) |
| *A61B 17/88* | (2006.01) |
| *A61F 2/08* | (2006.01) |
| *A61B 17/00* | (2006.01) |

(52) U.S. Cl.
CPC .......... *A61B 17/0401* (2013.01); *A61B 17/88* (2013.01); *A61F 2/0811* (2013.01);
(Continued)

(58) Field of Classification Search
CPC .... A61F 2002/0858; A61F 2002/30579; A61F 2002/30995; A61F 2002/4627;
(Continued)

(56) References Cited

U.S. PATENT DOCUMENTS

| | | | | |
|---|---|---|---|---|
| 5,849,004 A | * | 12/1998 | Bramlet | A61B 17/0401 606/310 |
| 8,551,171 B2 | * | 10/2013 | Johnson | A61B 17/844 606/279 |

(Continued)

FOREIGN PATENT DOCUMENTS

WO　　WO-2014174521 A1 * 10/2014　......... A61B 17/1617

*Primary Examiner* — Eduardo C Robert
*Assistant Examiner* — David C Comstock
(74) *Attorney, Agent, or Firm* — Riverside Law LLP

(57) ABSTRACT

Decortiating screws and insertion tools for implanting the decorticating screws including screws that anchor into a first and a second bone to fuse the two bones together. The screws include a rotatable bladed section to decorticate a joint space between the first and second bone. The screws also optionally include a cap to secure the screws in the bone and apply compression to the joint to be fused. In some embodiments, the decorticating screws are useful for sacro-iliac (SI) joint fusion.

33 Claims, 41 Drawing Sheets

100

146
156
153
158
154

(52) U.S. Cl.
CPC .............. *A61B 2017/00004* (2013.01); *A61F 2002/0858* (2013.01)

(58) Field of Classification Search
CPC ................. A61F 2/4611; A61F 2/0811; A61B 2017/00004; A61B 2017/681; A61B 17/0401; A61B 17/86; A61B 17/8605; A61B 17/8625; A61B 17/8685; A61B 17/8877; A61B 17/1617; A61B 17/68
USPC ....... 606/247, 301, 302, 304, 305, 306, 308, 606/310, 311, 312, 313, 314, 315, 316, 606/318, 319, 320, 323, 325, 326, 327, 606/328, 79, 80, 84, 85, 92, 93, 94, 99, 606/104, 86 A, 232
See application file for complete search history.

(56) References Cited

U.S. PATENT DOCUMENTS

| | | | | |
|---|---|---|---|---|
| 8,734,497 | B2 * | 5/2014 | Goel ................. | A61B 17/8685 606/313 |
| 2006/0276790 | A1 * | 12/2006 | Dawson ............... | A61F 2/4405 606/279 |
| 2007/0032790 | A1 * | 2/2007 | Aschmann ......... | A61B 17/7065 606/90 |
| 2009/0292316 | A1 * | 11/2009 | Hess .................. | A61B 17/7065 606/279 |
| 2013/0317509 | A1 * | 11/2013 | Anderson .......... | A61B 17/1617 606/82 |
| 2014/0031934 | A1 * | 1/2014 | Trieu ................ | A61B 17/8685 623/17.11 |
| 2014/0194930 | A1 * | 7/2014 | Hess .................. | A61B 17/7065 606/249 |
| 2014/0371795 | A1 * | 12/2014 | Hess .................. | A61B 17/7065 606/249 |
| 2015/0230844 | A1 * | 8/2015 | Ellis .................. | A61B 17/8635 606/316 |
| 2015/0313720 | A1 * | 11/2015 | Lorio .................. | A61B 17/863 623/17.11 |
| 2016/0242820 | A1 * | 8/2016 | Whipple ............ | A61B 17/8685 |
| 2016/0310188 | A1 * | 10/2016 | Marino ..................... | A61F 2/28 |
| 2017/0258498 | A1 * | 9/2017 | Redmond .......... | A61B 17/7055 |
| 2019/0090888 | A1 * | 3/2019 | Sand ................. | A61B 17/1615 |
| 2019/0231405 | A1 * | 8/2019 | Redmond .......... | A61B 17/7055 |
| 2020/0261240 | A1 * | 8/2020 | Mesiwala .......... | A61B 17/7055 |

* cited by examiner

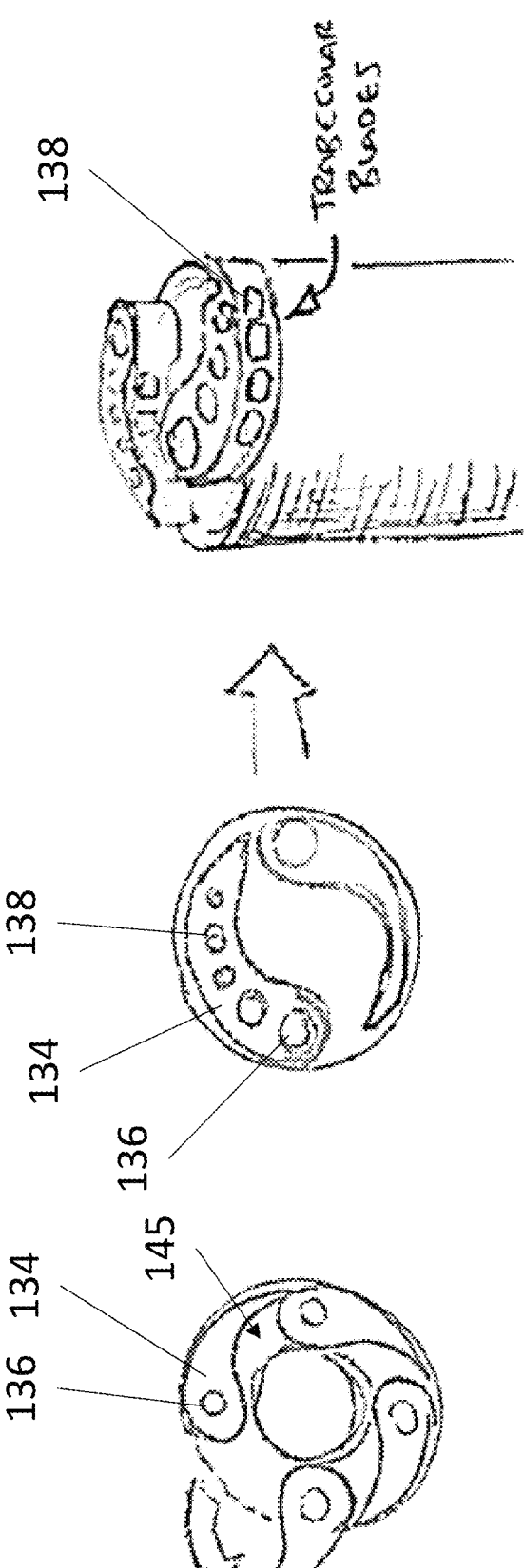
FIG. 3

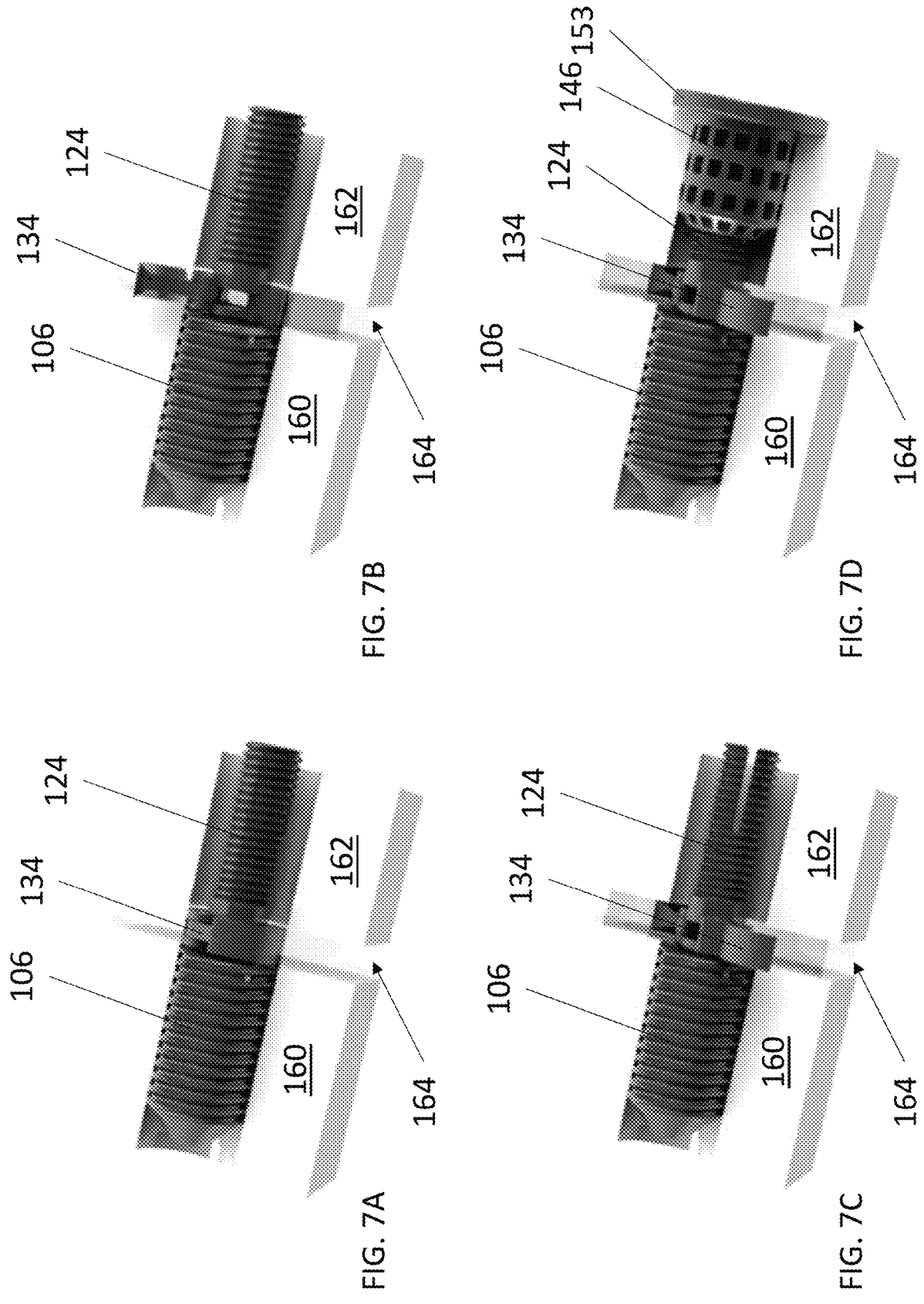

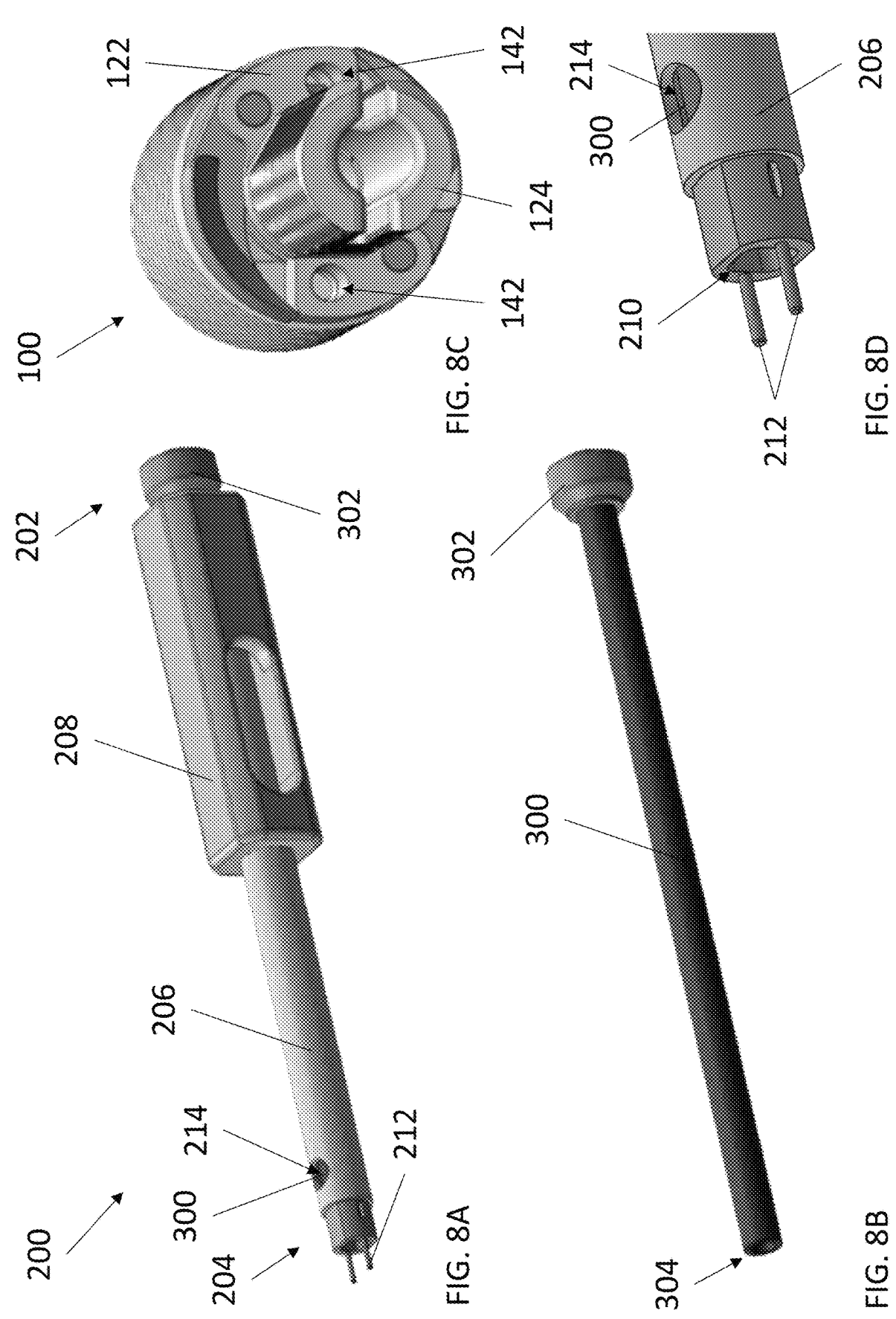

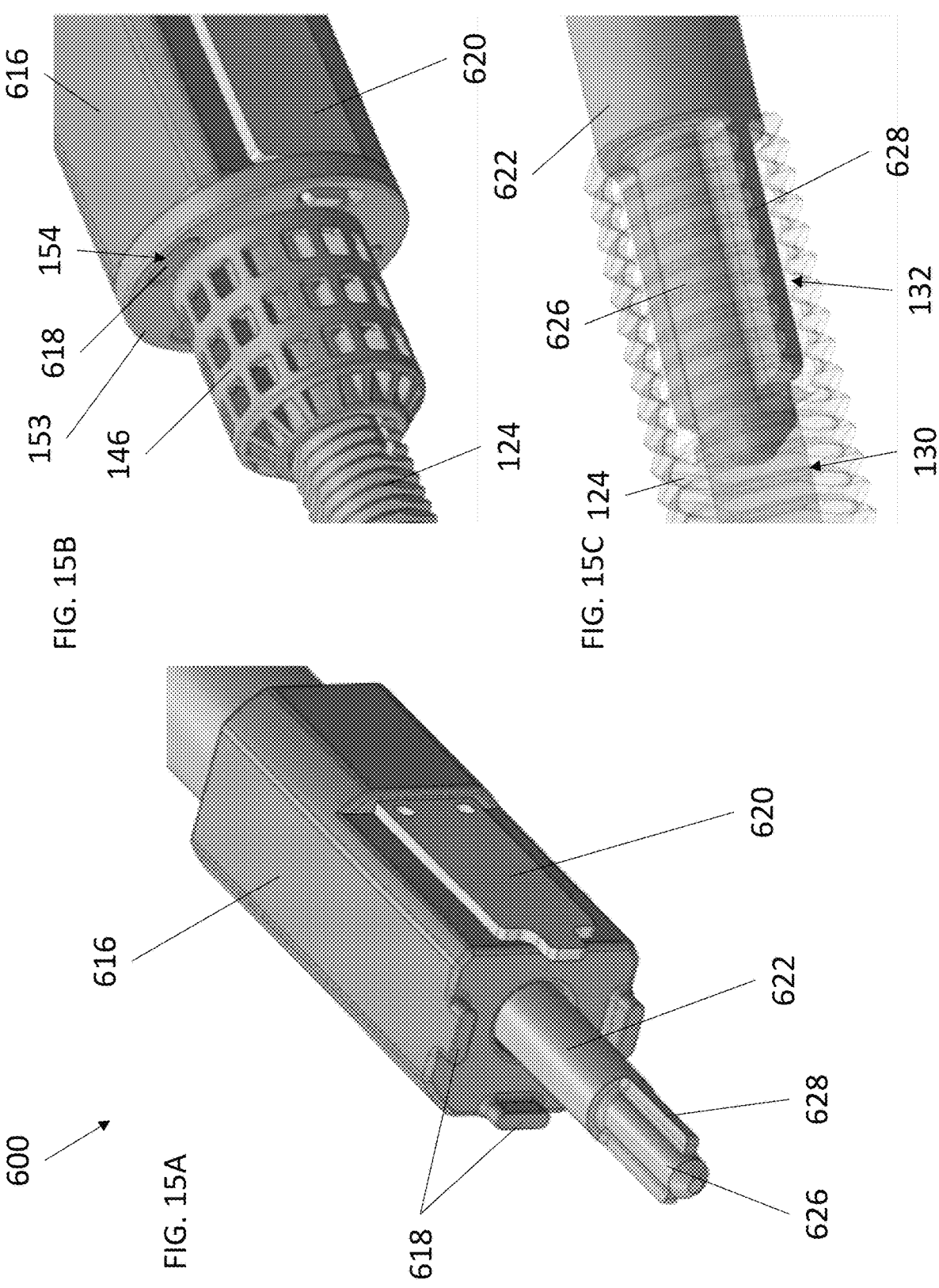

1000

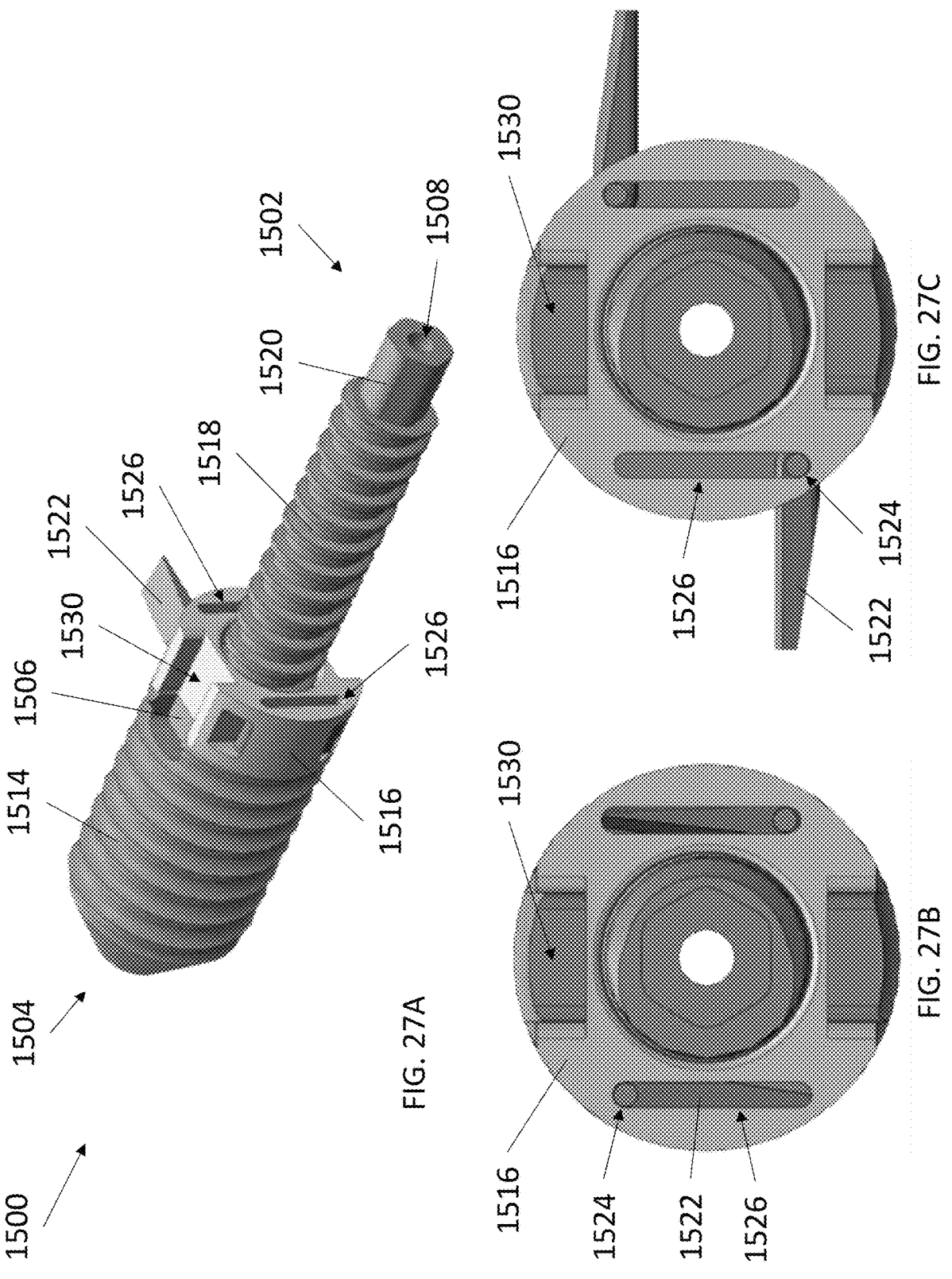

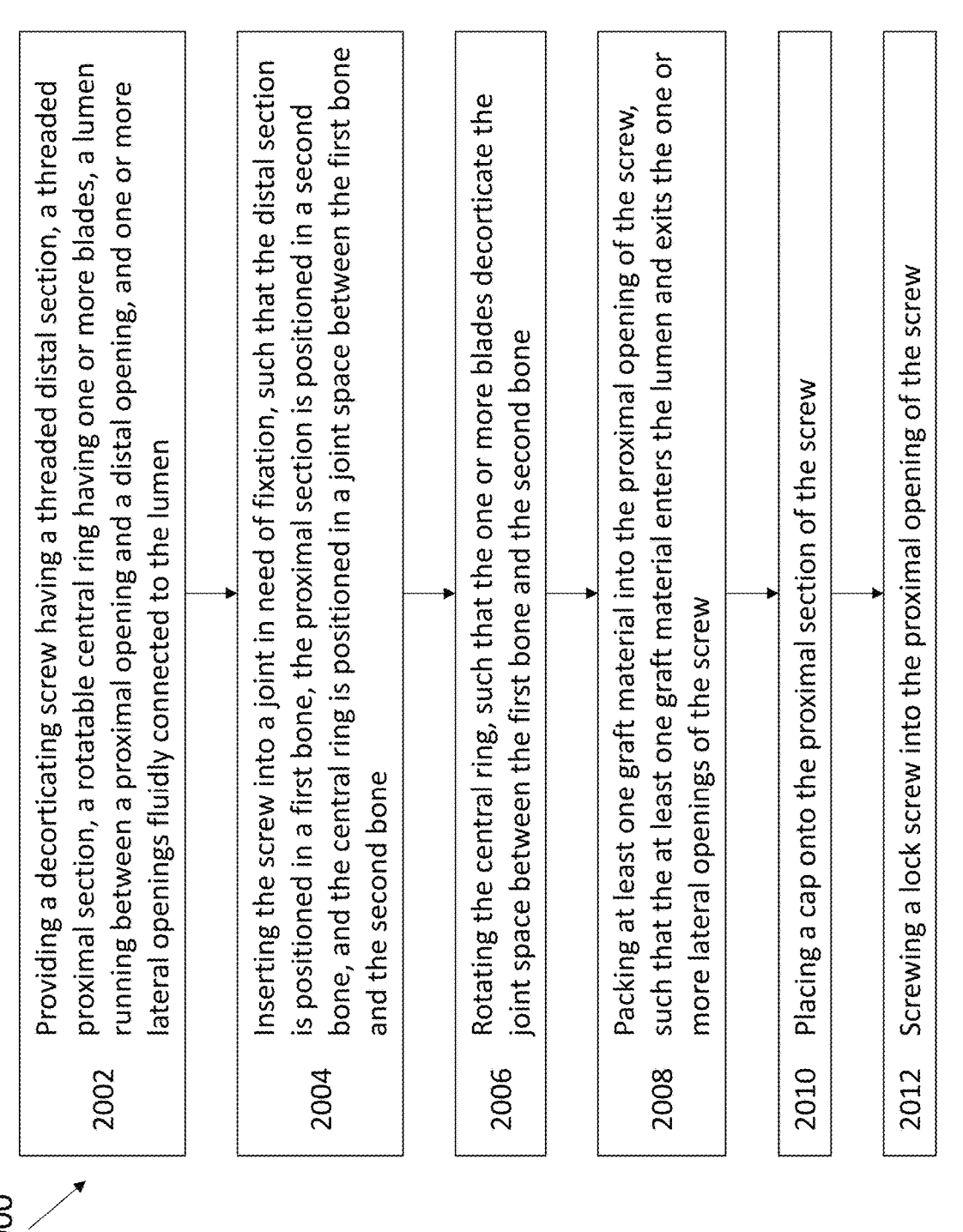

2000

2002  Providing a decorticating screw having a threaded distal section, a threaded proximal section, a rotatable central ring having one or more blades, a lumen running between a proximal opening and a distal opening, and one or more lateral openings fluidly connected to the lumen 2004  Inserting the screw into a joint in need of fixation, such that the distal section is positioned in a first bone, the proximal section is positioned in a second bone, and the central ring is positioned in a joint space between the first bone and the second bone 2006  Rotating the central ring, such that the one or more blades decorticate the joint space between the first bone and the second bone 2008  Packing at least one graft material into the proximal opening of the screw, such that the at least one graft material enters the lumen and exits the one or more lateral openings of the screw 2010  Placing a cap onto the proximal section of the screw 2012  Screwing a lock screw into the proximal opening of the screw

FIG. 40

DECORTICATING SCREW

CROSS-REFERENCE TO RELATED APPLICATIONS

This application is a national stage filing of International Patent Application No. PCT/US20/48516 filed on Aug. 28, 2020, which claim priority to U.S. Provisional Patent Application No. 62/893,672, filed Aug. 29, 2019, both of which are incorporated by reference herein in their entireties.

BACKGROUND OF THE INVENTION

Sacroiliac (SI) pain is a common cause of low back pain. One solution is minimally invasive SI joint fusion. However, existing SI joint fusion hardware inadequately addresses the SI joint space, resulting in deficient joint fusion and continued pain. True SI arthrodesis calls for the SI joint space to be decorticated and compressed in addition to the placement of stabilizing screws for positive long-term patient outcomes and significant reduction in pain scores.

Thus, there is a need in the art for improved screws that are capable of decorticating a joint space and applying compression to the fusion site. The present invention satisfies this need.

SUMMARY OF THE INVENTION

In one aspect, the present invention relates to a decorticating screw device, comprising: a substantially cylindrical body, the body having a distal threaded section, a proximal threaded section, a central ring having one or more decorticating elements.

In one embodiment, the screw further comprises a lumen running between a proximal opening and a distal opening.

In one embodiment, the screw device further comprises a cap having a threaded lumen sized to fit over the proximal threaded section of the body and a proximal lip having a diameter greater than a diameter of the cap.

In one embodiment, the central ring of the screw device is independently rotatable from the threaded distal section.

In one embodiment, the screw device further comprises one or more lateral openings fluidly connected to the lumen.

In one embodiment, the screw device comprises one or more cutting flutes at a distal end. In one embodiment, the screw device comprises one or more pointed tips at a distal end.

In one embodiment, the proximal threaded section comprises a threading selected from the group consisting of: knuckle threads, trapezoidal threads, square threads, and buttress threads. In one embodiment, the proximal threaded section comprises a rounded or tapered proximal end.

In one embodiment, the central ring is attached to the proximal section, such that the central ring and proximal section are independently rotatable from the threaded distal section. In one embodiment, the central ring is movable in proximal and distal directions to increase the reach of the one or more decorticating elements.

In one embodiment, the screw device comprises two or more external slots formed between the distal threaded section, the central ring, and the one or more decorticating elements, such that each external slot is sized to receive a pin of a screw driving device.

In one embodiment, the one or more decorticating elements each comprise one or more surface voids configured to accept graft material or tissue ingrowth. In one embodiment, the cap comprises one or more surface voids configured to accept graft material or tissue ingrowth.

In one embodiment, the cap comprises a thread-locking insert positioned at a proximal end of the threaded lumen. In one embodiment, the cap lip comprises a distal-facing surface having a rounded convex shape. In one embodiment, the cap comprises a locking nut in alignment with the threaded lumen of the cap, the locking nut being connected to the cap by one or more connecting bridges configured to break with an application of a torque on the locking nut.

In one embodiment, the one or more decorticating elements are moveable between a closed position and an open position. In one embodiment, the closed position positions the decorticating elements adjacent to the central ring such that they have a diameter substantially equal to a diameter of the threaded distal section, and wherein the open position positions the decorticating elements away from the central ring such that the decorticating elements extend beyond the diameter of the threaded distal section. In one embodiment, the one or more decorticating elements are hingedly connected to the central ring along an axis that is in parallel with a long axis of the body and are laterally swung from the closed position to the open position. In one embodiment, the one or more decorticating elements are hingedly connected to the central ring along an axis that is perpendicular to a long axis of the body and splay outwards from the closed position to the open position. In one embodiment, the one or more decorticating elements are flexible wire blades retracted into the central ring in a closed position and are pushable outwards from the central ring to the open position. In one embodiment, the one or more decorticating elements are sheathed within the central ring in a closed position and are slideable outwards from the closed position to the open position. In one embodiment, the one or more decorticating elements are at least partially pliable and are bendable from a closed position to an open position. In one embodiment, the one or more decorticating elements comprises at least one serration.

In one embodiment, the threaded proximal section has diameter that is less than a diameter of the threaded distal section. In one embodiment, the diameter of the cap is substantially equal to a diameter of the threaded distal section. In one embodiment, the device further comprises a lock screw having a diameter larger than a diameter of the screw device lumen, the lock screw being drivable into the proximal opening of the screw device to expand a proximal end of the screw device.

In one embodiment, the screw has a length between about 10 mm and about 100 mm. In one embodiment, the screw has an outer diameter between about 5 mm and about 50 mm.

In another aspect, the present invention relates to a method of fusing a joint between a first bone and a second bone, comprising the steps of: providing a decorticating screw having a threaded distal section, a threaded proximal section, a rotatable central ring having one or more blades, a lumen running between a proximal opening and a distal opening, and one or more lateral openings fluidly connected to the lumen; inserting the screw into a joint in need of fixation, such that the distal section is positioned in a first bone, the proximal section is positioned in a second bone, and the central ring is positioned in a joint space between the first bone and the second bone; rotating the central ring, such that the one or more blades decorticate the joint space between the first bone and the second bone; packing at least one graft material into the proximal opening of the screw, such that the at least one graft material enters the lumen and exits the one or more lateral openings of the screw; placing a cap onto the proximal section of the screw; and screwing a lock screw into the proximal opening of the screw.

In one embodiment, the graft material is selected from the group consisting of: autologous bone grafts, allogeneic bone grafts, xenogeneic bone grafts, hydroxyapatite, calcium phosphate, calcium sulphate, bioactive glass, polymers, cements, and combinations thereof.

BRIEF DESCRIPTION OF THE DRAWINGS

The following detailed description of exemplary embodiments of the invention will be better understood when read in conjunction with the appended drawings. It should be understood, however, that the invention is not limited to the precise arrangements and instrumentalities of the embodiments shown in the drawings.

FIG. 2A is a cross-sectional side view of a distal screw component attached to a proximal screw component. FIG. 2B is a proximal view of a distal screw component.

FIG. 2C is a partially transparent view of a proximal screw component. FIG. 2D is a partially transparent view of a distal screw component attached to a proximal screw component.

FIG. 3 depicts various varieties and views of exemplary screw blades

FIG. 6 is a schematic depicting a cross-sectional side view of an exemplary screw inserted into a first bone, a second bone, and a joint space in between.

FIG. 7A through FIG. 7D depict a sequence of decortication using an exemplary screw.

FIG. 8A through FIG. 8D depict an exemplary screw driving tool. FIG. 8A is a perspective view of the screw driving tool. FIG. 8B is a perspective view of an exemplary locking tube. FIG. 8C is a perspective view of an exemplary screw highlighting engagement points with a screw driving tool. FIG. 8D is a magnified view of the distal tip of a screw driving tool.

FIG. 10A is a perspective view of the blade deploying tool. FIG. 10B is a perspective view of an exemplary screw highlighting engagement points with a blade deploying tool.

FIG. 10C is a magnified view of the distal tip of a blade deploying tool.

FIG. 12A is a perspective view of the graft funnel tool engaged to an exemplary screw. FIG. 12B is a partially transparent magnified view of the graft funnel tool engaged to the screw.

FIG. 15A through FIG. 15C depict magnified views of an exemplary cap driving tool. FIG. 15A is a magnified view of the distal end of the cap driving tool. FIG. 15B is a magnified view of the cap driver engaged to the cap of an exemplary screw.

FIG. 15C is a partially transparent magnified view of the cap driving tool engaged to the proximal stem of the screw.

FIG. 16A is a perspective view of the lock screw driver engaged to an exemplary screw. FIG. 16B is a magnified view of the lock screw driver engaged to the screw.

FIG. 18A is a perspective view of the blade deploying tool. FIG. 18B is a magnified view of the distal end of the blade deploying tool.

FIG. 21A is a magnified view of the distal end of the blade deploying tool. FIG. 21B is a perspective view of the screw with blades held in blade retainers. FIG. 21C is a perspective view of the screw with blades released from the blade retainers.

FIG. 27A through FIG. 27C depict an exemplary screw. FIG. 27A is a perspective view of the screw. FIG. 27B is a proximal view of the screw with blades in a closed position. FIG. 27C is a proximal view of the screw with blades in an open position.

FIG. 29A through FIG. 29C depict the screw with blades in a closed position. FIG. 29D through FIG. 29F depict the screw with blades in an open position.

FIG. 31 depicts an exemplary decorticating screw having a tapered or rounded proximal shaft lead in.

FIG. 40 is a flowchart of an exemplary method of using a decorticating screw.

DETAILED DESCRIPTION

Figures 1A, 1B:
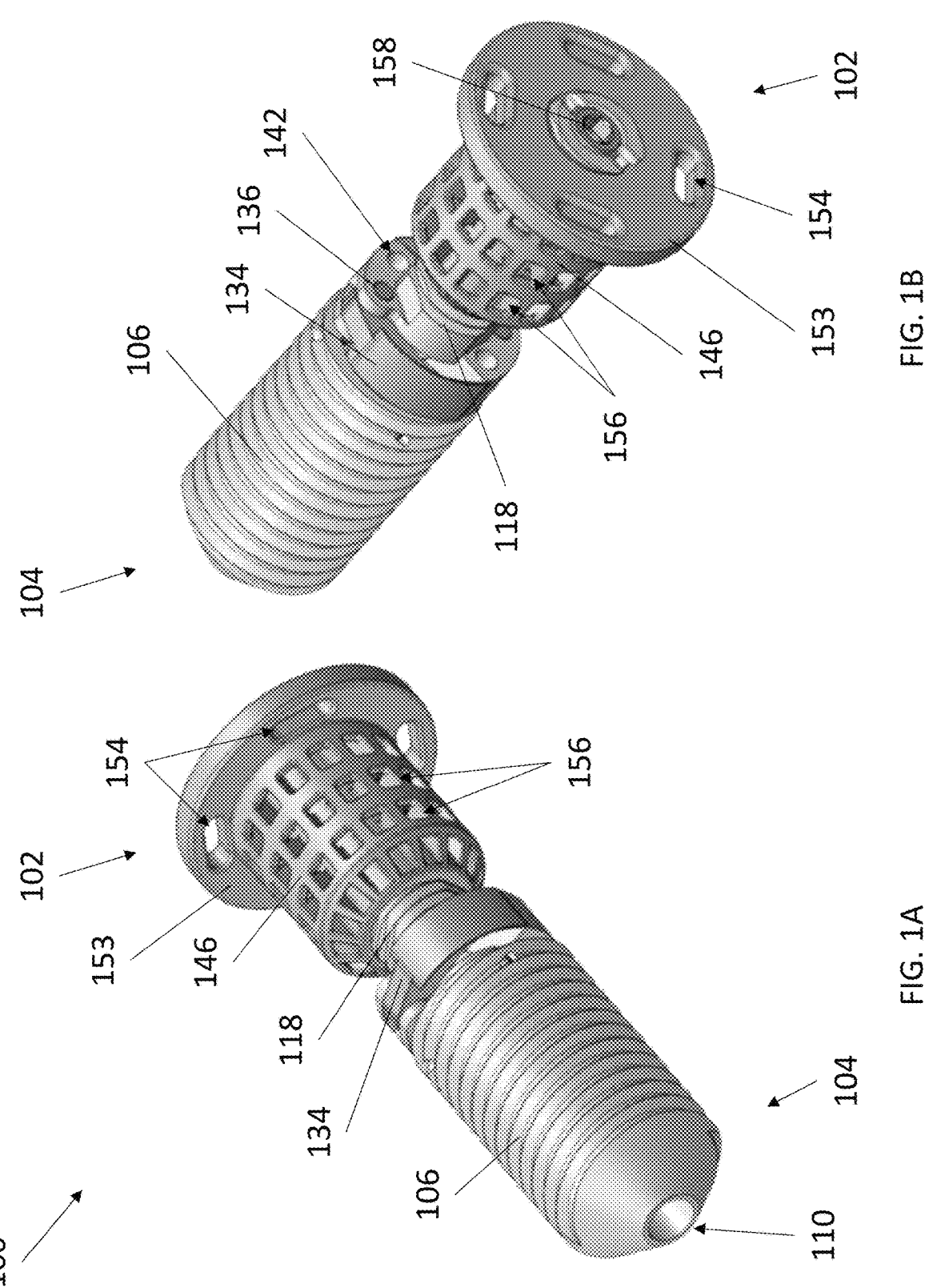
FIG. 1A and FIG. 1B depict perspective views of an exemplary screw.
Figures 2A, 2B:
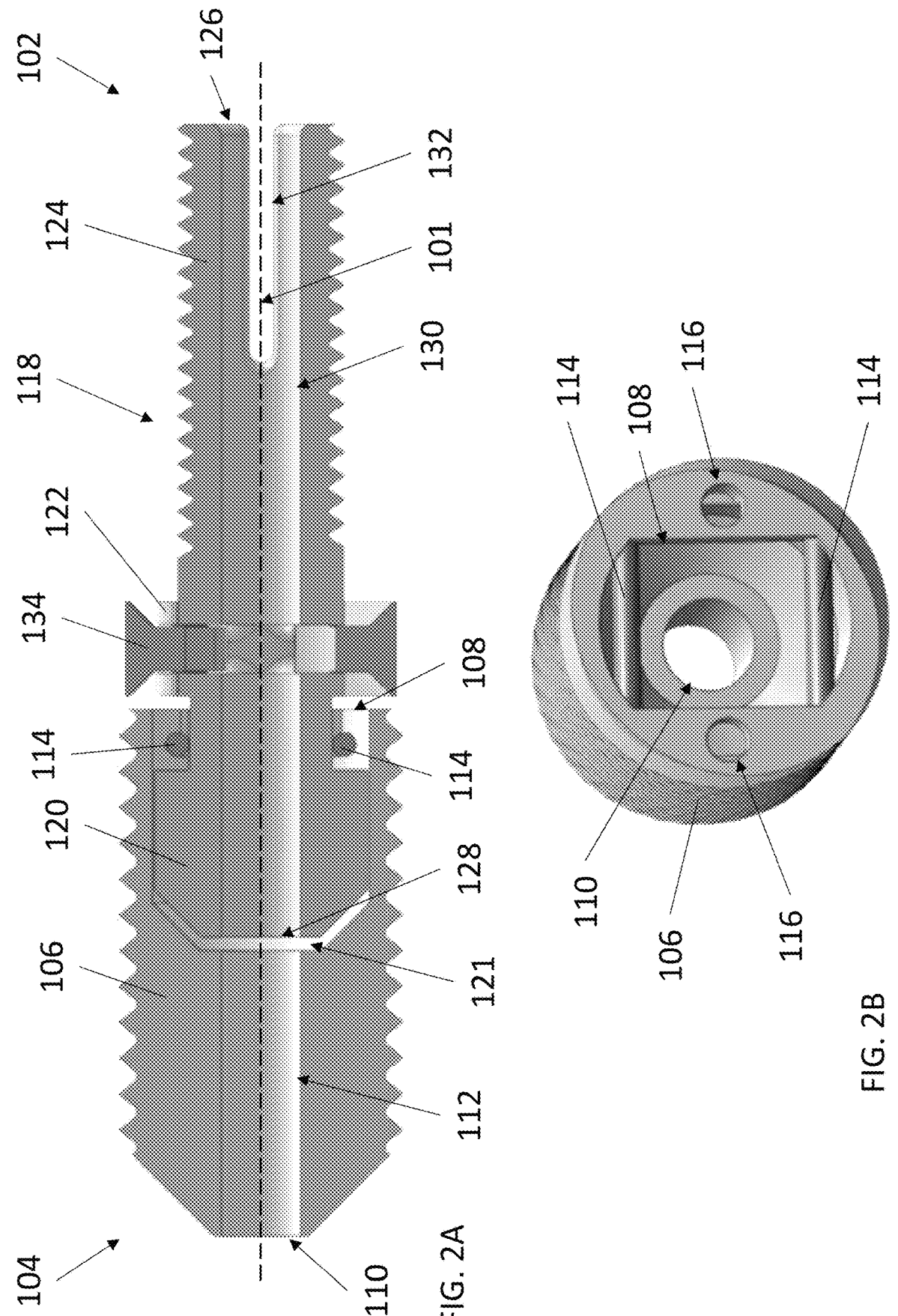
FIG. 2A through FIG. 2D depict various views of an exemplary screw assembly.
Figures 2C, 2D:
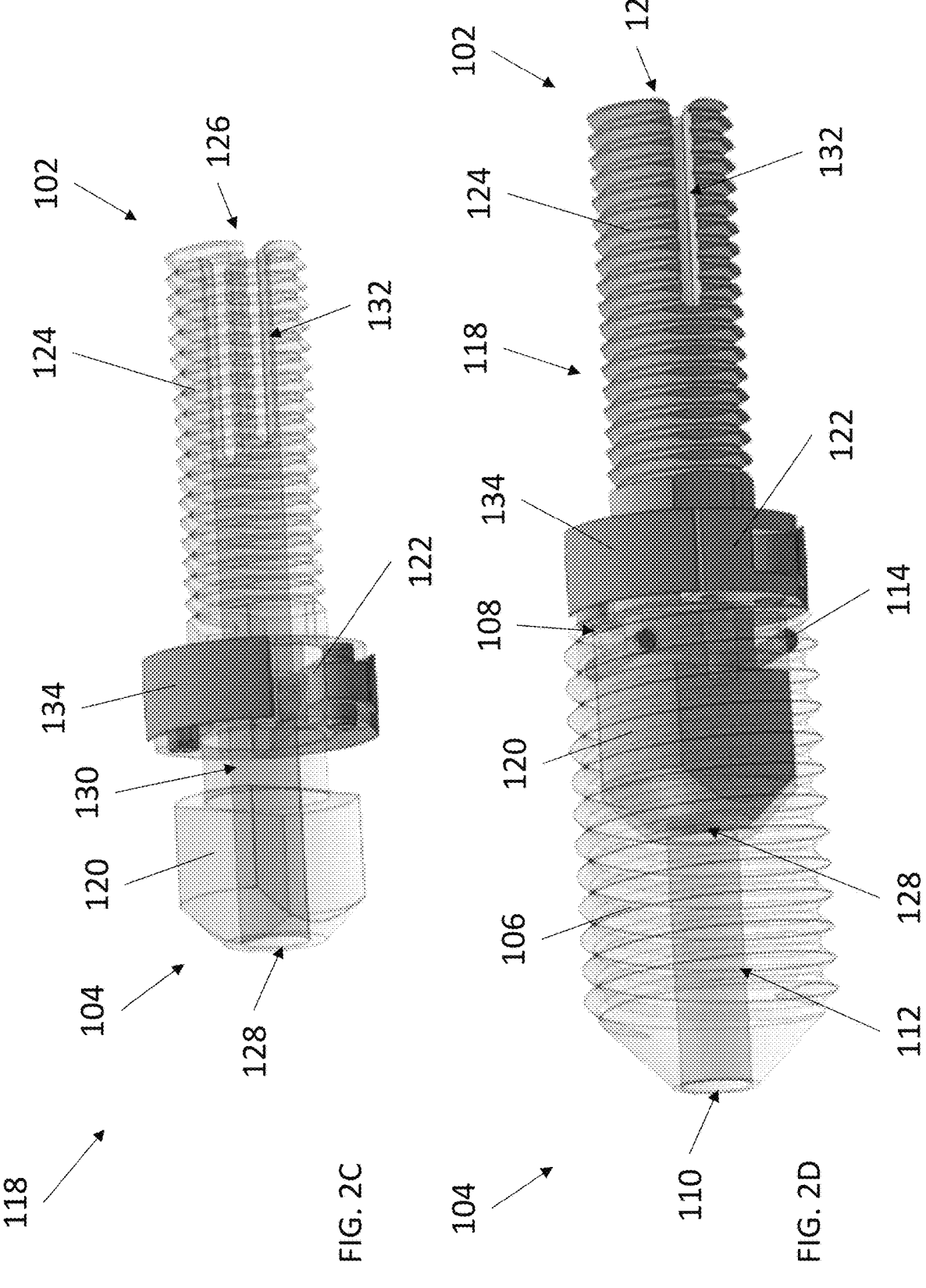

The present invention provides decorticating screws and insertion tools for implanting the decorticating screws. The screws anchor into a first and a second bone to fuse the two bones together. The screws include a rotatable bladed section to decorticate a joint space between the first and second bone. The screws also optionally include a cap to secure the screws in the bone and apply compression to the joint to be fused. In some embodiments, the decorticating screws are useful for sacroiliac (SI) joint fusion.

Definitions

It is to be understood that the figures and descriptions of the present invention have been simplified to illustrate elements that are relevant for a clear understanding of the present invention, while eliminating, for the purpose of clarity, many other elements typically found in the art. Those of ordinary skill in the art may recognize that other elements and/or steps are desirable and/or required in implementing the present invention. However, because such elements and steps are well known in the art, and because they do not facilitate a better understanding of the present invention, a discussion of such elements and steps is not provided herein. The disclosure herein is directed to all such variations and modifications to such elements and methods known to those skilled in the art.

Unless defined elsewhere, all technical and scientific terms used herein have the same meaning as commonly understood by one of ordinary skill in the art to which this invention belongs. Although any methods and materials similar or equivalent to those described herein can be used in the practice or testing of the present invention, the exemplary methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, and ±0.1% from the specified value, as such variations are appropriate.

Throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6, etc., as well as individual numbers within that range, for example, 1, 2, 2.7, 3, 4, 5, 5.3, 6, and any whole and partial increments there between. This applies regardless of the breadth of the range.

First Decorticating Screw

Referring now to FIG. 1A and FIG. 1B, an exemplary decorticating screw 100 is now described. Screw 100 comprises a proximal end 102 and a distal end 104, wherein a distal screw 106 is engaged to the distal end of a proximal screw 118. A cap 146 fits over the proximal end of proximal screw 118 and is locked in place by a lock screw 158.

Referring now to FIG. 2A through FIG. 2D, distal screw 106 and proximal screw 118 are now described. Distal screw 106 comprises a substantially cylindrical shape having a tapered distal end ending in distal opening 110, a proximal end having a proximal opening 108, and a lumen 112 extending between distal opening 110 and proximal opening 108. Distal screw 106 comprises a threaded exterior. In some embodiments, distal screw 106 comprises one or more cutting flutes at the distal end, such that distal screw 106 is self-tapping. Visible in FIG. 2B, the proximal end of distal screw 106 comprises two or more pin slots 116. Distal screw 106 further comprises one or more pins 114 extending laterally across proximal opening 108.

Proximal screw 118 comprises a substantially cylindrical shape with a lumen 130 extending between a proximal opening 126 and a distal opening 128, wherein lumen 130 is alignable with lumen 112 to form a single continuous lumen. The continuous lumen can be sized to fit commonly used guide wires and Steinmann pins. Proximal screw 118 has three regions: a distal nose 120, a central ring 122, and a proximal stem 124. Distal nose 120 has a diameter sized to fit through proximal opening 108 of distal screw 106. Inserting pins 114 through distal screw 106 prevents distal nose 120 from backing out of distal screw 106. In this manner, proximal screw 118 is free to rotate about common axis 101 shared between proximal screw 118 and distal screw 106 while engaged to distal screw 106. In some embodiments, distal nose 120 is sized slightly shorter than proximal opening 108 of distal screw 106 such that a gap 121 is provided, permitting proximal screw 118 with room to shift in proximal and distal directions. Proximal stem 124 has a threaded exterior and at least one stem slot 132 extending from proximal opening 126 in a distal direction. In some embodiments, proximal stem 124 has a diameter smaller than a diameter of distal screw 106.

Figures 4A, 4B:
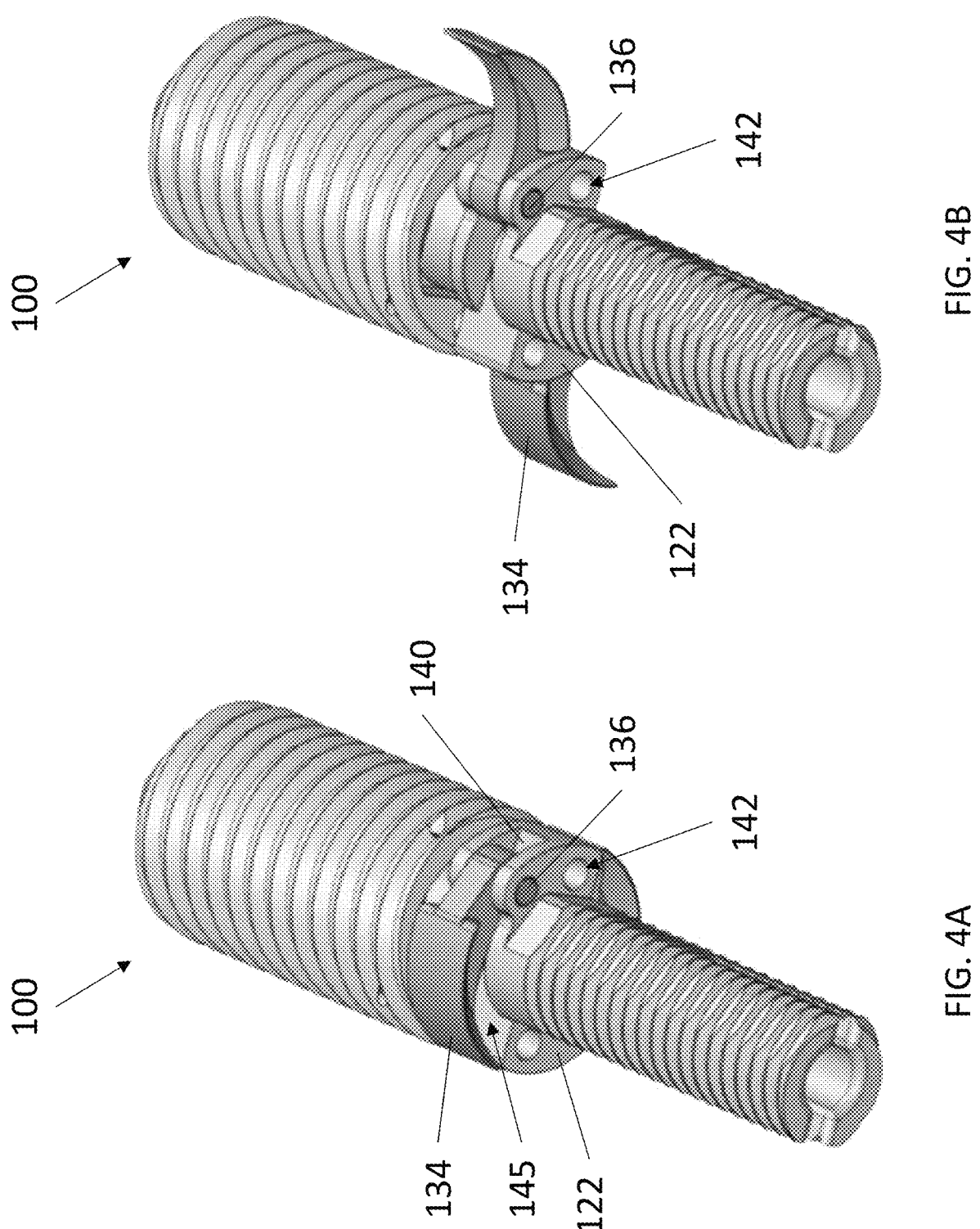
FIG. 4A and FIG. 4B depict an exemplary screw with blades in a closed (FIG. 4A) and an open (FIG. 4B) position.

Central ring 122 comprises one or more blades 134. Each blade 134 has a curved construction ending in a sharp or beveled tip. Blades 134 can have a solid construction, or have one or more voids 138 positioned on a side or throughout (FIG. 3). Voids 138 can include graft material or encourage ingrowth of tissue. Each blade 134 is hingedly connected to central ring 122 by a pin 136, such that blade 134 can fold against central ring 122 in a closed position (FIG. 4A) and swing away from central ring 122 in an open position (FIG. 4B). The hinged connection is in parallel alignment with a long axis of screw 100. In a closed position, blade 134 forms a tool space 145 with central ring 122. Central ring 122 can further comprise a blade stop 140 adjacent to pin 136, which is a surface that limits the swinging angle of blade 134. Central ring 122 further comprises two or more pin slots 142. Pin slots 142 are alignable with pin slots 116 of distal screw 106 to form a continuous lumen. In some embodiments, central ring 122 has a diameter substantially equal to a diameter of distal screw 106.

Figures 5A, 5B:
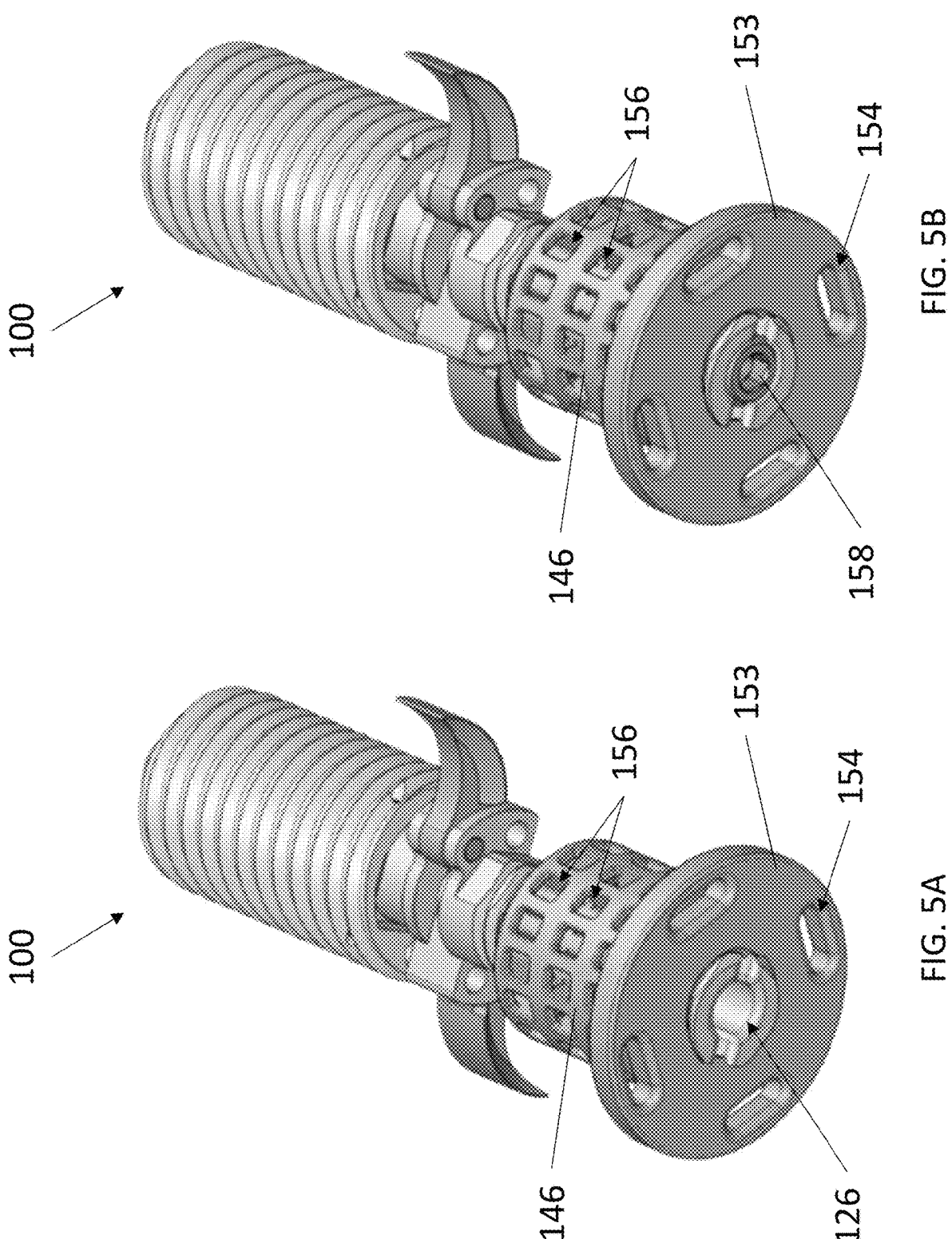
FIG. 5A and FIG. 5B depict an exemplary screw with a cap component attached (FIG. 5A) and cap component with a lock screw attached (FIG. 5B).
Figure 6:
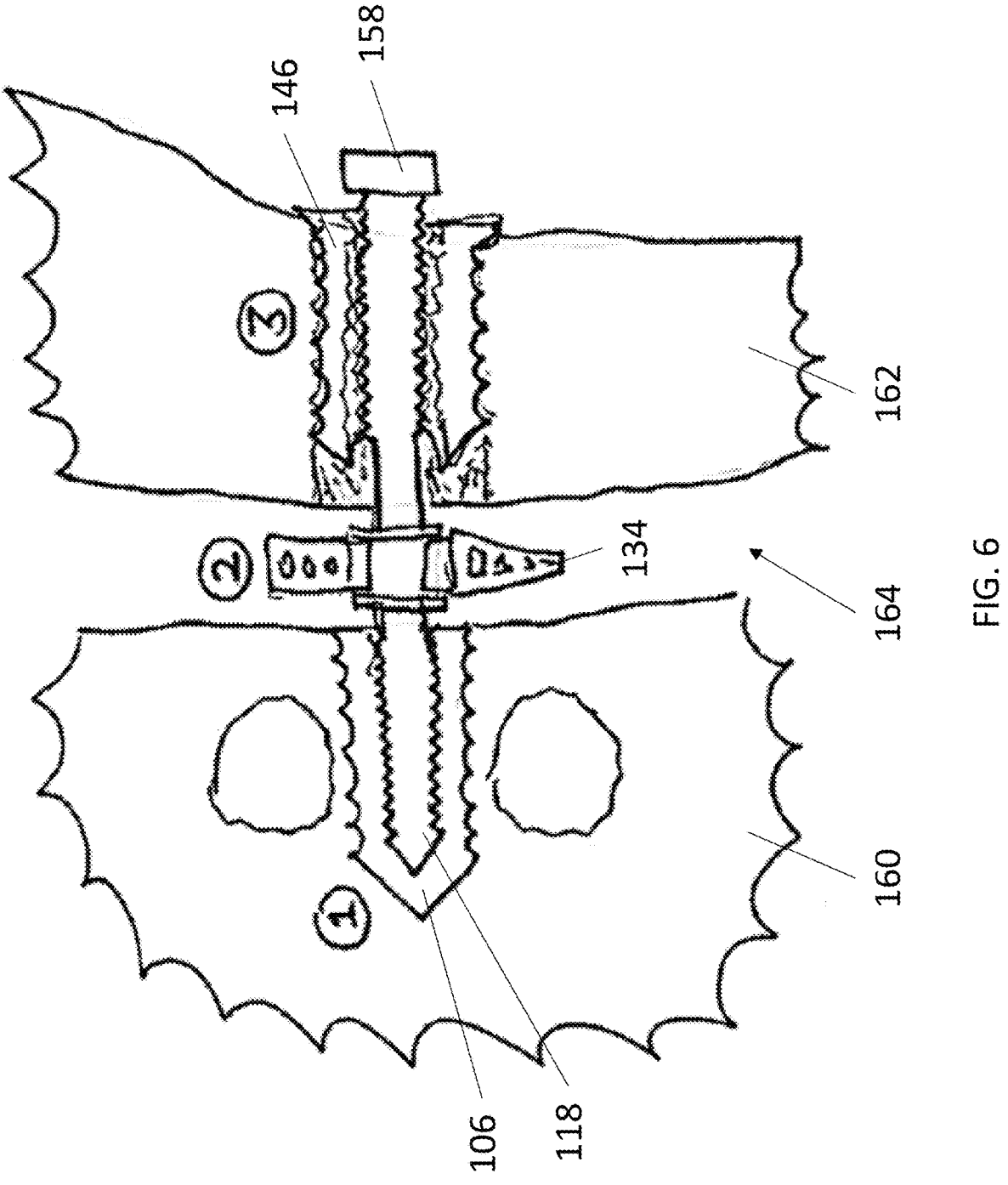

Referring now to FIG. 5A and FIG. 5B, cap 146 and lock screw 158 are now described. Cap 146 comprises a substantially cylindrical shape having a lumen extending between proximal opening and a distal opening. The lumen of cap 146 has a threaded surface sized to screw onto the threaded exterior of proximal stem 124. Cap 146 has a proximal surface having one or more tab slots 154. The proximal surface comprises a lip 153 that extends beyond a diameter of cap 146 to catch onto a bone surface and aid in bone compression. Cap 146 has an exterior surface that can include one or more apertures 156 that can accept graft material or tissue ingrowth. In some embodiments, cap 146 has a diameter substantially equal to a diameter of distal screw 106. Lock screw 158 is sized to screw within proximal opening 126 of proximal stem 124. Lock screw 158 comprises an outer diameter that is slightly larger than the inner diameter of lumen 130, such that inserting lock screw 158 into proximal opening 126 expands proximal stem 124 and prevents cap 146 from loosening.

In essence, screw 100 is a decorticating screw device comprising a substantially cylindrical body, the body having a distal threaded section, a proximal threaded section, a central ring having one or more decorticating elements, and a lumen running between a proximal opening and a distal opening, and one or more lateral openings fluidly connected to the lumen; and a cap having a threaded lumen sized to fit over the proximal threaded section of the body and a proximal lip having a diameter greater than a diameter of the cap; wherein the central ring is independently rotatable from the threaded distal section. In one embodiment, the screw comprises one or more cutting flutes at a distal end. In one embodiment, the central ring is attached to the proximal section, such that the central ring and proximal section are independently rotatable from the threaded distal section. In one embodiment, the central ring is movable in proximal and distal directions to increase the reach of the one or more blades. In one embodiment, the one or more blades each comprise one or more surface voids configured to accept graft material or tissue ingrowth. In one embodiment, the cap comprises one or more surface voids configured to accept graft material or tissue ingrowth. In one embodiment, the one or more blades are moveable between a closed position and an open position. In one embodiment, the closed position positions the blades adjacent to the central ring such that they have a diameter substantially equal to a diameter of the threaded distal section, and wherein the open position positions the blades away from the central ring such that the blades extend beyond the diameter of the threaded distal section.

Referring now to FIG. 6 and FIG. 7A through FIG. 7D, the operation of screw 100 is now described. As described elsewhere herein, screw 100 is provided for the locking of a first bone to a second bone. To this end, screw 100 comprises three distinct regions: a first region defined by distal screw 106 that secures into a first bone 160; a second region defined by central ring 122 and blades 134 that decorticates a joint space 164 between first bone 160 and second bone 162; and a third region defined by the proximal end of proximal screw 118 and cap 146 that secures into a second bone 162. FIG. 7A through FIG. 7D depict the sequence in which screw 100 locks a first bone 160 to a second bone 162. In FIG. 7A, the blades 134 are retracted to allow for insertion of screw 100, wherein screw 100 is screwed into first bone 160 such that distal screw 106 resides within first bone 160, proximal stem 124 resides within second bone 162, and central ring 122 is positioned within joint space 164. In FIG. 7B, blades 134 are deployed from central ring 122. In FIG. 7C, proximal screw 118 is rotated to decorticate joint space 164 using blades 134. The aforementioned gap 121 permits proximal screw 118 to be shifted in proximal and distal directions to allow blades 134 to decorticate closer to first bone 160 and second bone 162. In some embodiments, decorticated material can be removed by suction through the apertures, lumens, and proximal opening of screw 100. In FIG. 7D, the decorticated space is packed with graft material and screw 100 is capped with cap 146, compressing second bone 162 against first bone 160 with lip 153. Lock screw 158 can then be optionally inserted into proximal opening 126 to expand proximal stem 124 and prevent cap 146 from loosening.

Several tools are provided to drive screw 100 and to manipulate its subcomponents. Referring now to FIG. 8A and FIG. 8B, an exemplary screw driving tool 200 is now described. Screw driving tool 200 comprises an elongate shaft 206 having a lumen 214 running throughout. Shaft 206 has a handle 208 positioned at proximal end 202, pins 212 positioned at a distal end 204, and a distal opening 210 sized to fit proximal stem 124 of proximal screw 118. As described elsewhere herein, central ring 122 comprises pin slots 142 that are alignable with pin slots 116 of distal screw 106 to form a continuous lumen. Pins 212 are sized to fit within the continuous lumen formed by pin slots 142 and pin slots 116. Locking tube 300 comprises an elongate hollow cylindrical construction with a grip 302 at a proximal end and a threaded distal opening 304 sized to screw onto the threaded exterior of proximal stem 124. Locking tube 300 has an outer diameter sized to fit within lumen 214 of screw driving tool 200.

Figures 9A, 9B:
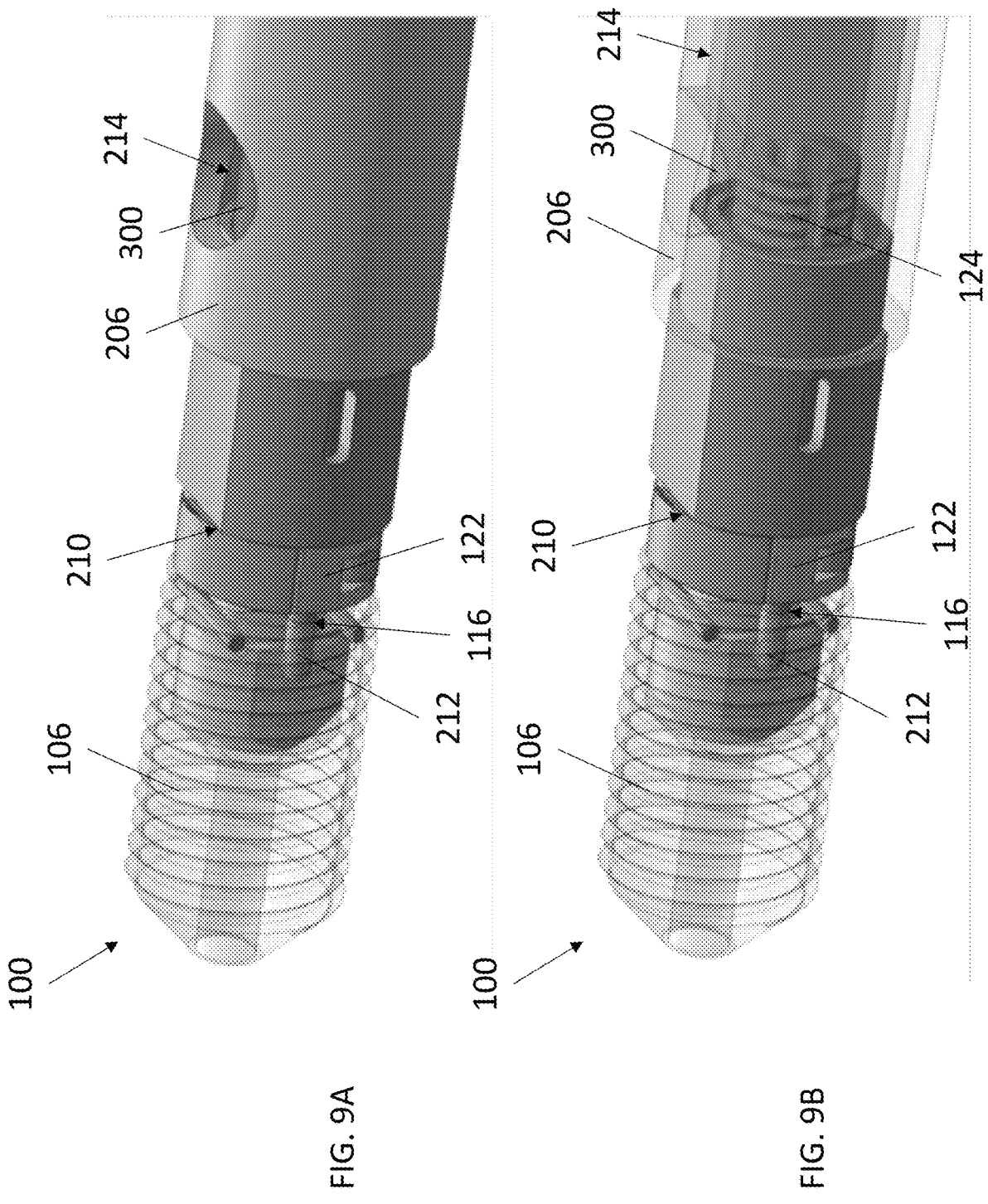
FIG. 9A and FIG. 9B depict partially transparent views of the engagement of an exemplary screw driving tool with an exemplary screw.

Visible in FIG. 9A and FIG. 9B, screw driving tool 200 secures to screw 100 by fitting distal opening 210 of shaft 206 over proximal stem 124 such that pins 212 are inserted through pin slots 142 and pin slots 116. Screw driving tool 200 is locked to screw 100 by screwing distal opening 304 of locking tube 300 onto proximal stem 124. Screw driving tool 200 can thereby simultaneously drive distal screw 106 and proximal screw 118 into a target site.

Figures 10A, 10B, 10C:
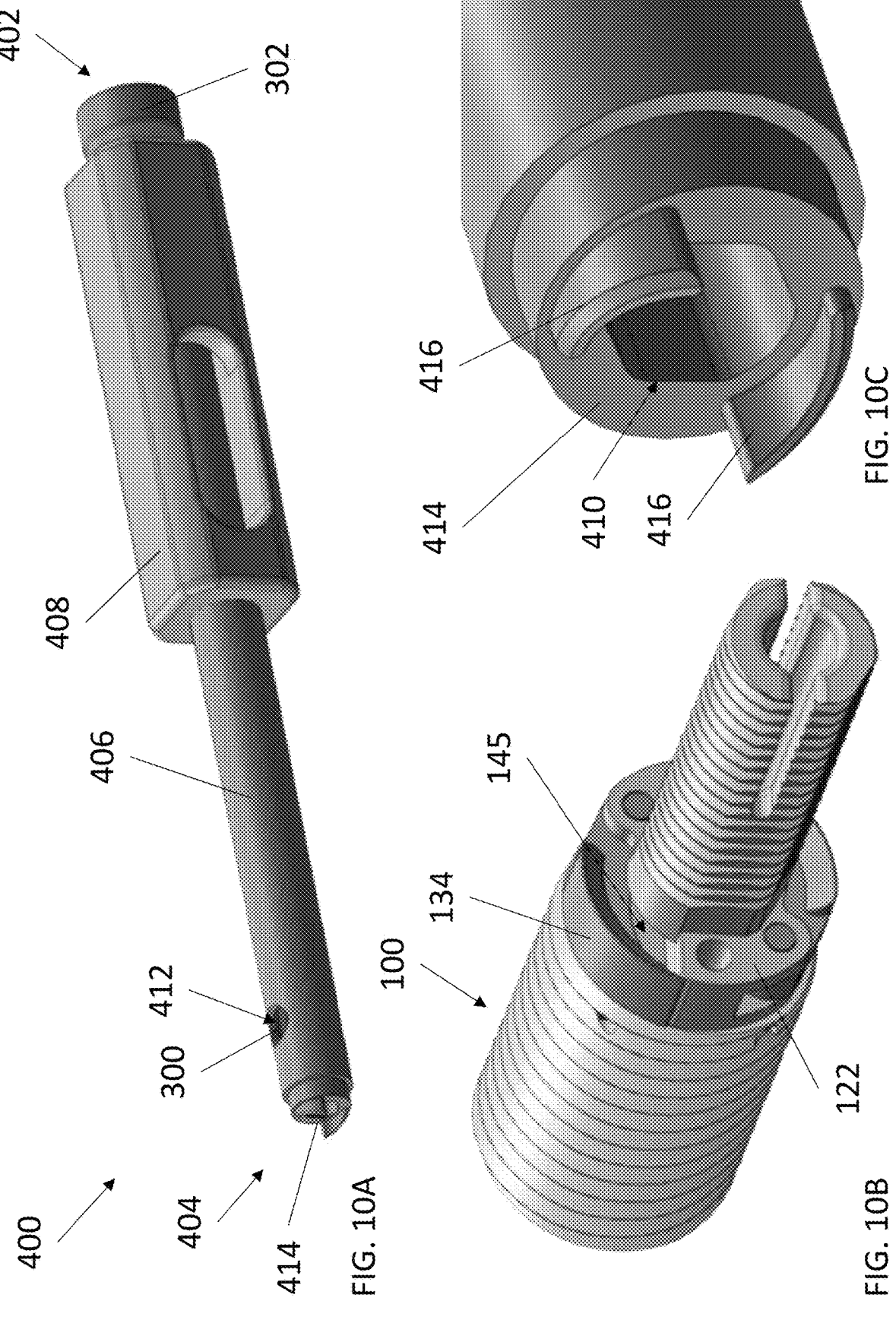
FIG. 10A through FIG. 10C depict an exemplary blade deploying tool.

Referring now to FIG. 10A through FIG. 10C, an exemplary blade deploying tool 400 is now described. Blade deploying tool 400 comprises an elongated shaft 406 having a handle 408 at a proximal end 402 and a blade engaging tip 414 at a distal end 404. Blade deploying tool 400 further comprises a lumen 412 extending between a proximal opening and a distal opening 410, wherein lumen 412 is sized to fit locking tube 300 described elsewhere herein and distal opening 410 is sized to fit over proximal stem 124 of proximal screw 118. Blade engaging tip 414 comprises one or more curved ramps 416 sized to fit within tool space 145 between blade 134 and central ring 122 of screw 100.

Figures 11A, 11B, 11C:
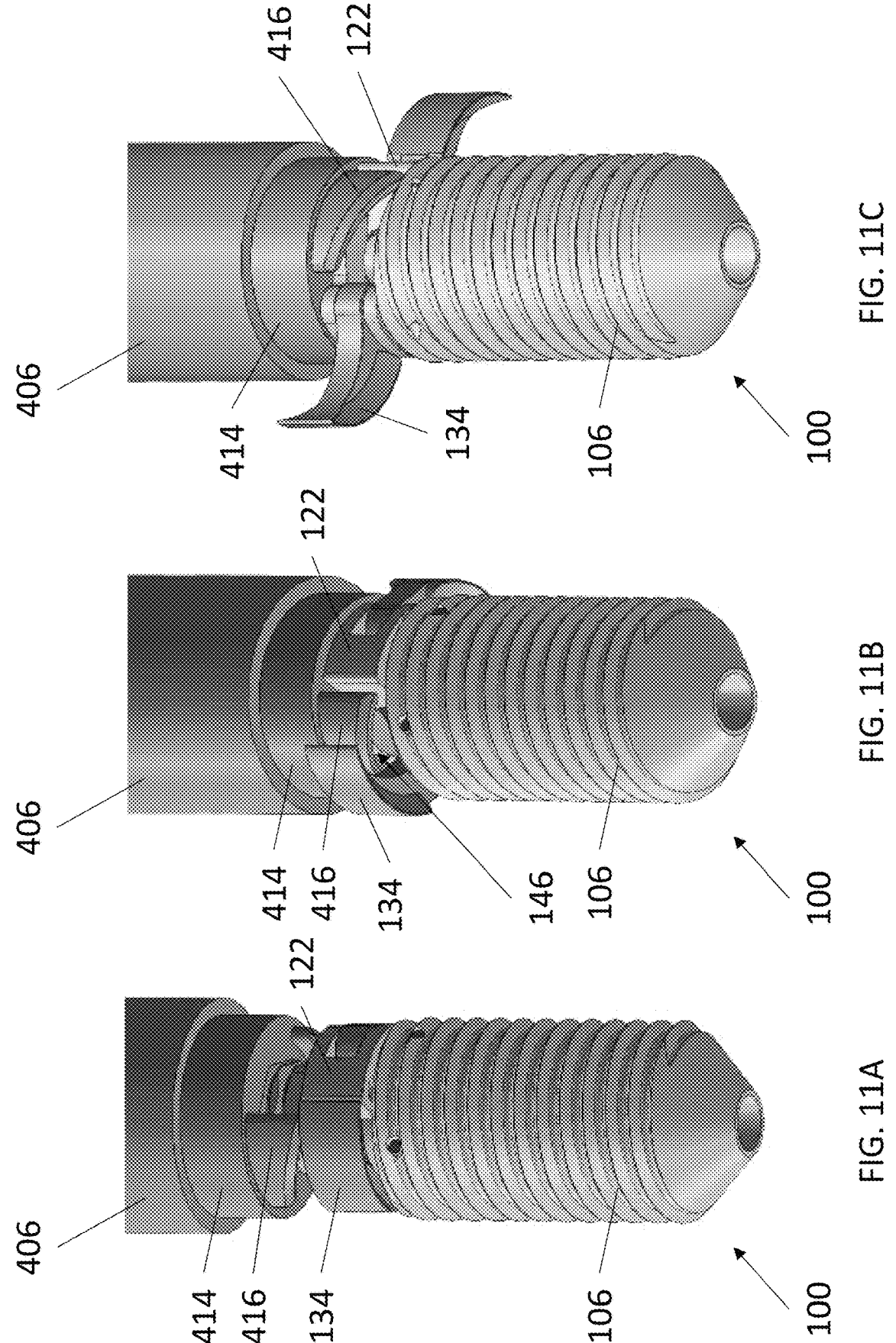
FIG. 11A through FIG. 11C depict a sequence of deploying the blades of an exemplary screw using an exemplary blade deploying tool.

FIG. 11A through FIG. 11C illustrate the operation of blade deploying tool 400. Between FIG. 11A and FIG. 11B, blade deploying tool 400 is fit over proximal stem 124 of proximal screw 118, wherein each curved ramp 416 is wedged into tool space 145 to force blades 134 away from central ring 122. While not visible, locking tube 300 is inserted through lumen 412 of blade deploying tool 400 and screwed onto proximal stem 124 to secure blade deploying tool 400 to screw 100. In FIG. 11C, blade deploying tool 400 is rotated, wherein blades 134 catch onto surrounding material and are forced fully open to carve out the surrounding material. It should be understood that blade deploying tool 400 is secured only to proximal screw 118, such that rotating blade deploying tool 400 rotates only proximal screw 118 while distal screw 106 remains stationary.

Figures 12A, 12B:
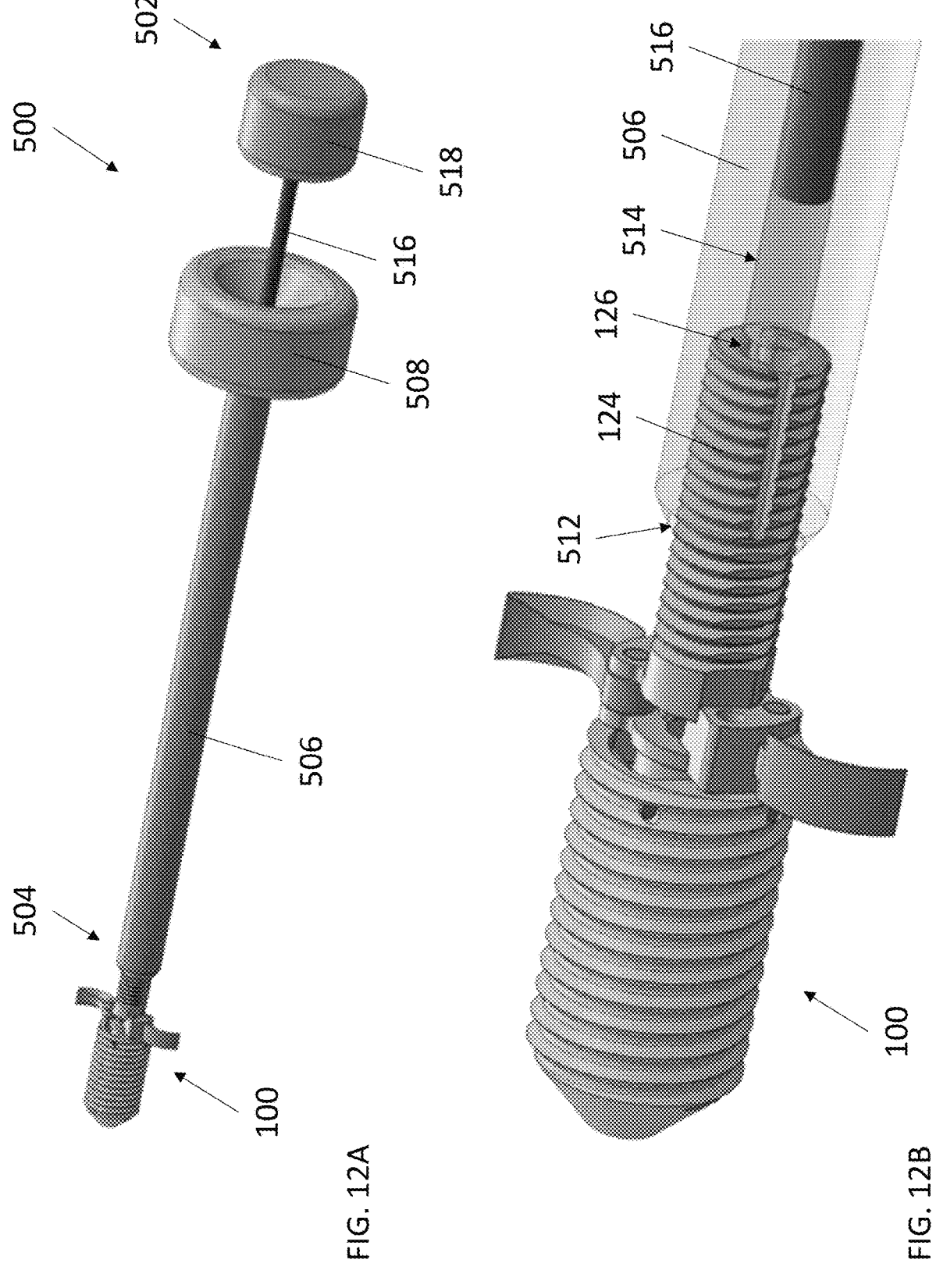
FIG. 12A and FIG. 12B depict an exemplary graft funnel tool.
Figures 13A, 13B, 13C:
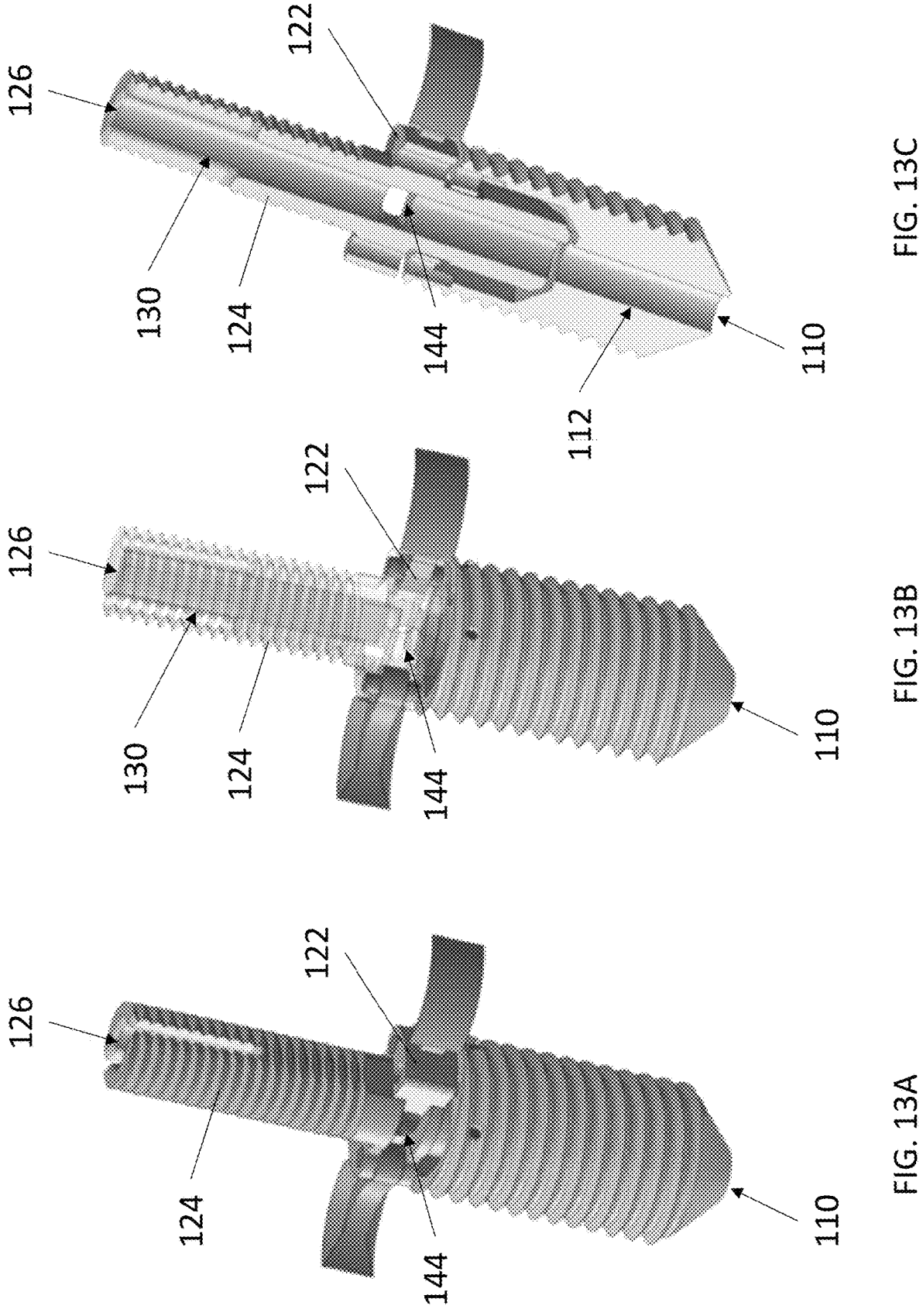
FIG. 13A through FIG. 13C depict various views of an exemplary screw highlighting graft entry and exit points.
Figure 14:
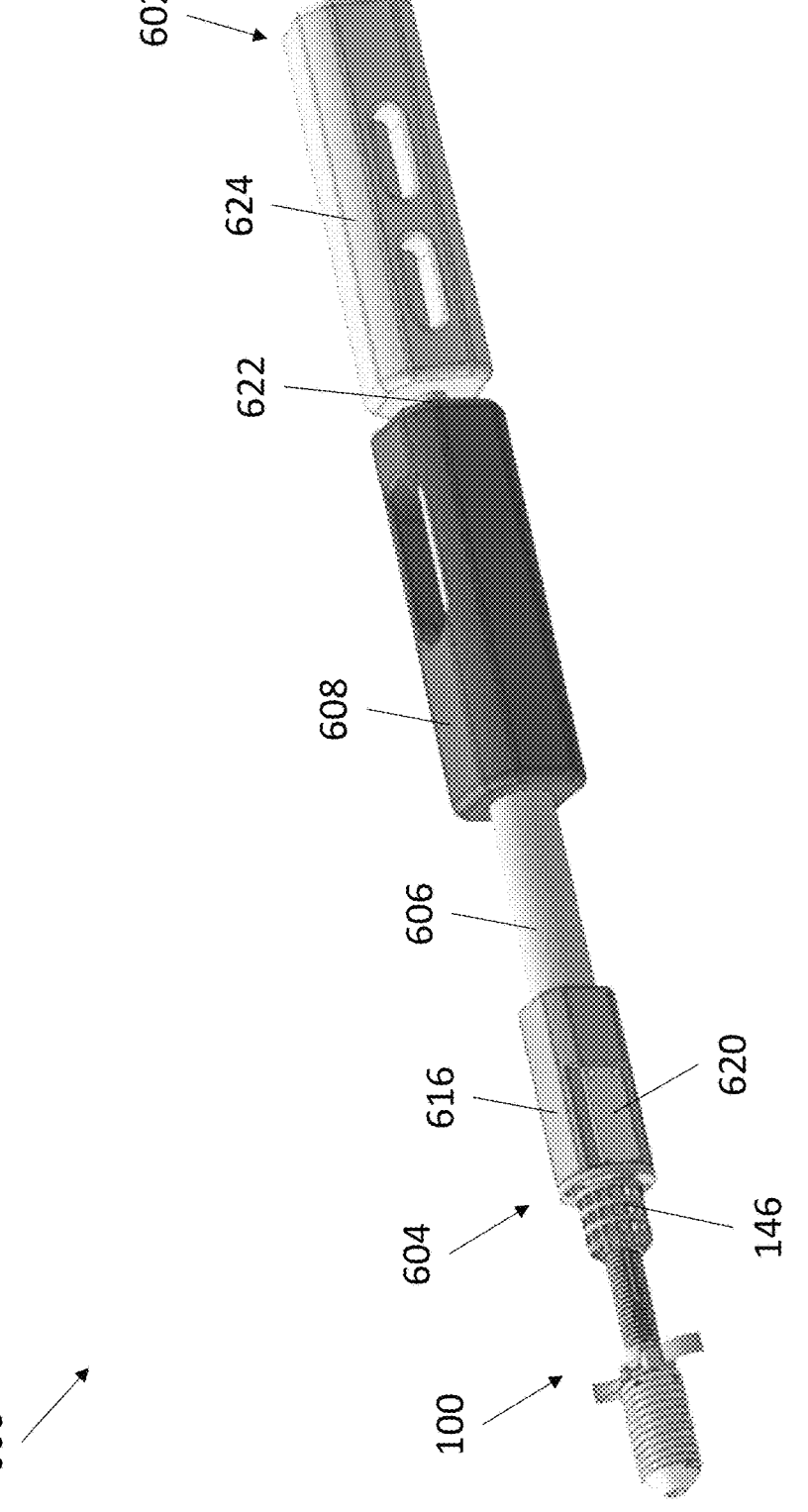
FIG. 14 depicts an exemplary cap driving tool engaged to an exemplary screw.

Referring now to FIG. 12A and FIG. 12B, an exemplary graft funnel tool 500 is now described. Graft funnel tool 500 comprises a shaft 506 having a handle 508 at a proximal end 502 and a distal opening 512 at a distal end 504. Graft funnel tool 500 further comprises a lumen 514 running between a proximal opening and distal opening 512, wherein lumen 514 is sized to fit packing rod 516. Packing rod 516 can include a grip 518 positioned at a distal end. Distal opening 512 comprises a threaded interior sized to screw onto the threaded exterior of proximal stem 124. In this manner, graft material can be inserted into the proximal opening of graft funnel tool 500 and packed into screw 100 using packing rod 516. The pathways for graft material is shown in FIG. 13A through FIG. 13C. Graft material enters proximal opening 126 of screw 100 and fills lumen 130 of proximal screw 118 and lumen 112 of distal screw 106. Graft material is able to exit screw 100 and fill any adjacent spaces by way of distal opening 110 and apertures 144 positioned on central ring 122. In particular, apertures 144 provide access to the space decorticated by blades 134 for the inflow of graft material.

Referring now to FIG. 14 and FIG. 15A through FIG. 15C, an exemplary cap driving tool 600 is now described. Cap driving tool 600 has a proximal end 602 and a distal end 604 and comprises an outer shaft 606 having a proximal handle 608, a distal cap driver 616, and a lumen extending between a proximal opening and a distal opening. Cap driver 616 comprises one or more tabs 618, each tab 618 sized to fit within a tab slot 154 on cap 146. Cap driver 616 further comprises one or more spring clips 620, each spring clip 620 also having a tab sized to fit within a tab slot 154 on cap 146. Spring clip 620 provides a spring force that releasably secures cap driver 616 to a proximal end of cap 146. Cap driving tool 600 further comprises an inner shaft 622 positioned within the lumen of outer shaft 606, inner shaft 622 comprising a proximal grip 624 and a distal tip 626. Distal tip 626 is sized to fit within lumen 130 of proximal screw 118. Distal tip 626 further comprises distal tabs 628 that are sized to fit within stem slots 132 of proximal screw 118. Cap driving tool 600 thereby engages screw 100 by linking distal tip 626 of inner shaft 622 with proximal screw 118 and cap driver 616 of outer shaft 606 with cap 146. Inner shaft 622 and proximal screw 118 are held stationary, enabling outer shaft 606 to be actuated to drive cap 146 onto proximal stem 124.

Figures 16A, 16B:
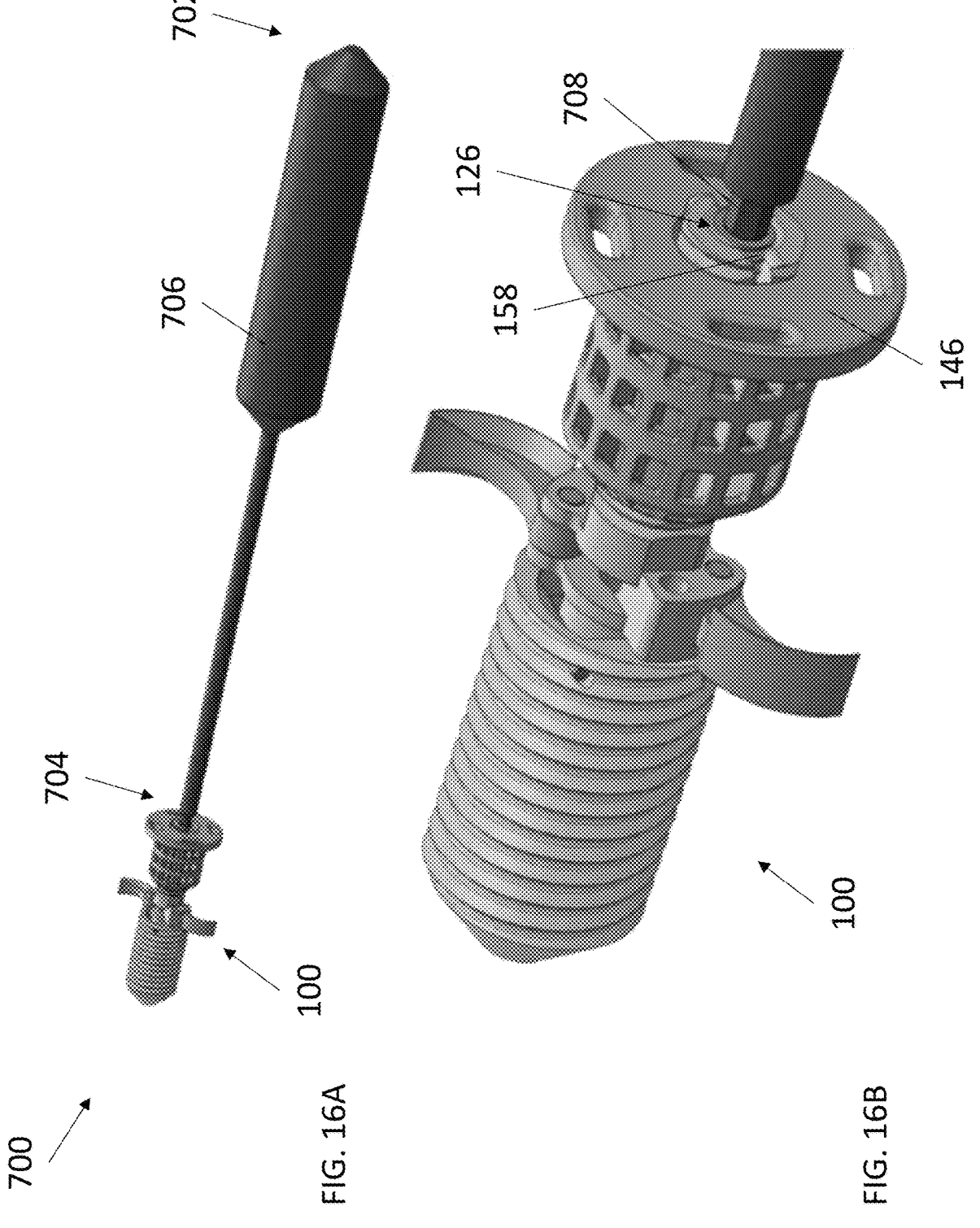
FIG. 16A and FIG. 16B depict an exemplary lock screw driver.

Referring now to FIG. 16A and FIG. 16B, an exemplary lock screw driver 700 is now described. Lock screw driver 700 has a proximal end 702 and a distal end 704 and comprises a distal handle 706 and a proximal screw bit 708 sized to fit lock screw 158. Lock screw driver 700 can be used to drive lock screw 158 into proximal opening 126, whereupon lock screw 158 slightly expands the proximal end of proximal stem 124 to prevent cap 146 from loosening and detaching from screw 100.

Second Decorticating Screw

Referring now to FIG. 17A through FIG. 19B, another exemplary screw 100 is depicted having a proximal screw 800 with central ring 802 and a complementary blade deploying tool 900. Similar to central ring 122 of proximal screw 118, central ring 802 comprises one or more hingedly connected blades 804. Central ring 802 further comprises curved slots 806 positioned adjacent to each blade 804. Blades 804 are deployable using blade deploying tool 900, which has a proximal end 902 and a distal end 904 and comprises a distal shaft 906 having a lumen 908 running between a proximal opening 910 and a distal cavity 912. Adjacent to distal cavity 912, blade deploying tool 900 comprises one or more pins 914, each pin sized to fit within a curved slot 806. Blade deploying tool 900 further comprises tongs 916 having a distal end sized to fit within lumen 908 and dimensioned to couple with a proximal opening and stem slots of proximal screw.

Figures 17A, 17B:
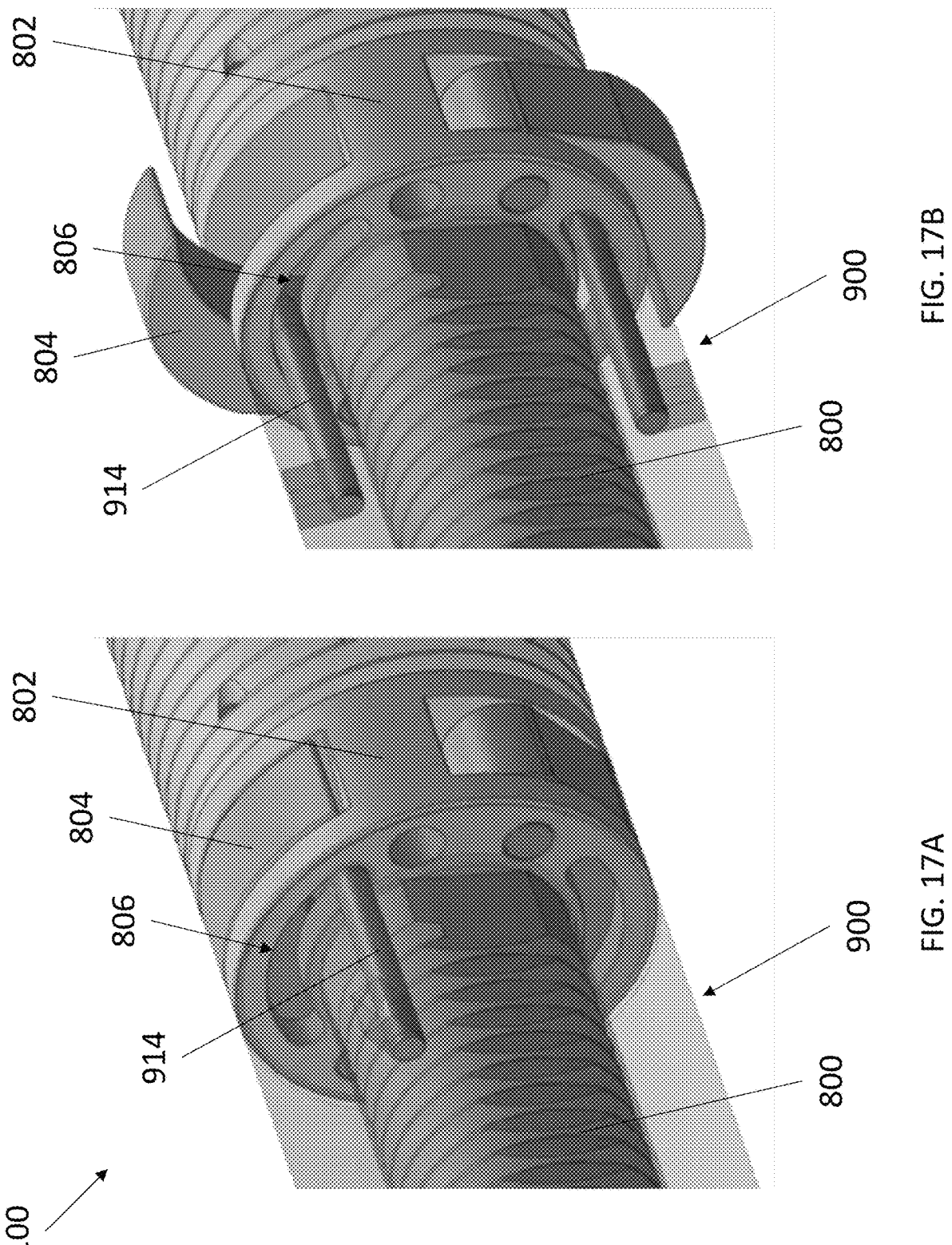
FIG. 17A and FIG. 17B depict partially transparent magnified views of an exemplary blade deploying tool engaged to an exemplary screw.
Figures 18A, 18B:
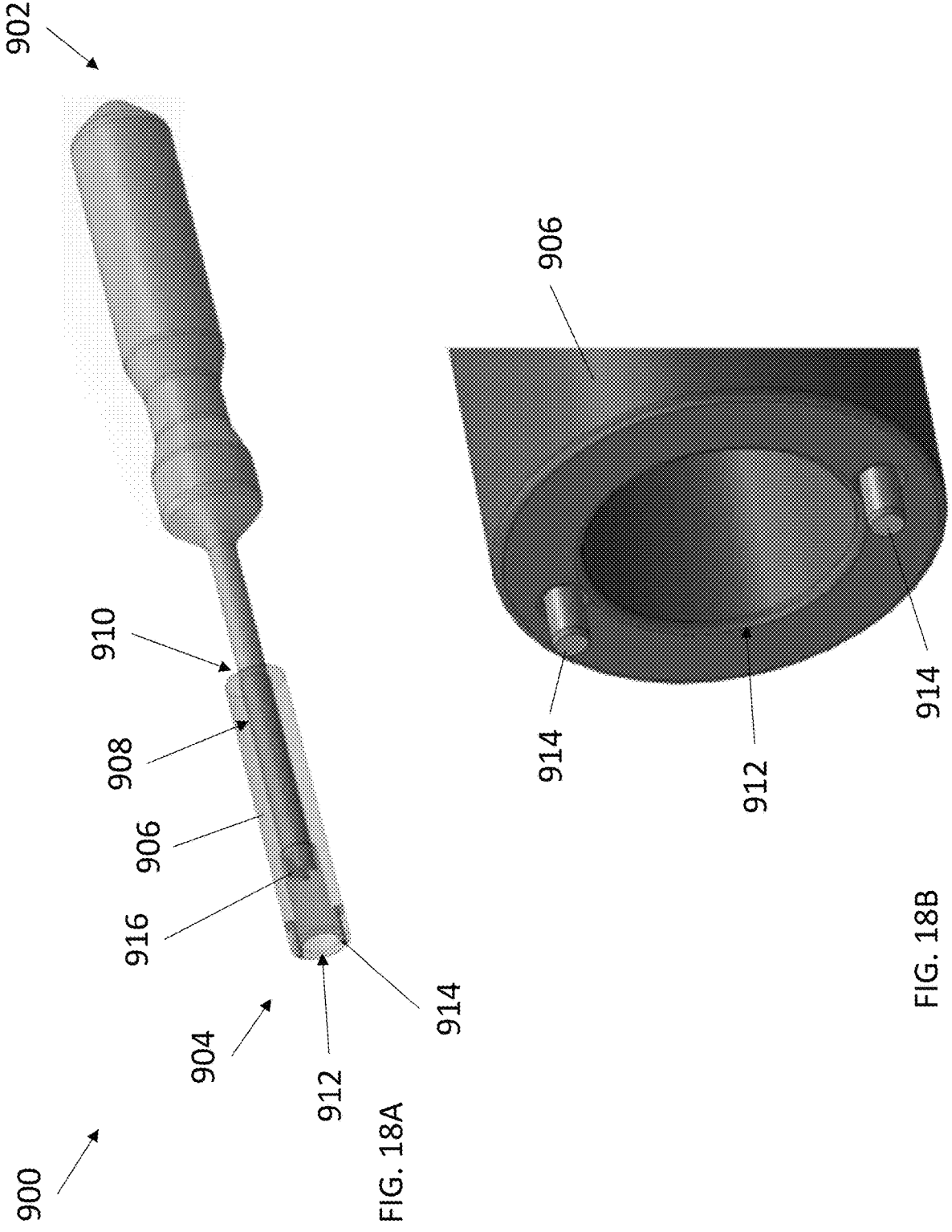
FIG. 18A and FIG. 18B depict an exemplary blade deploying tool.
Figures 19A, 19B:
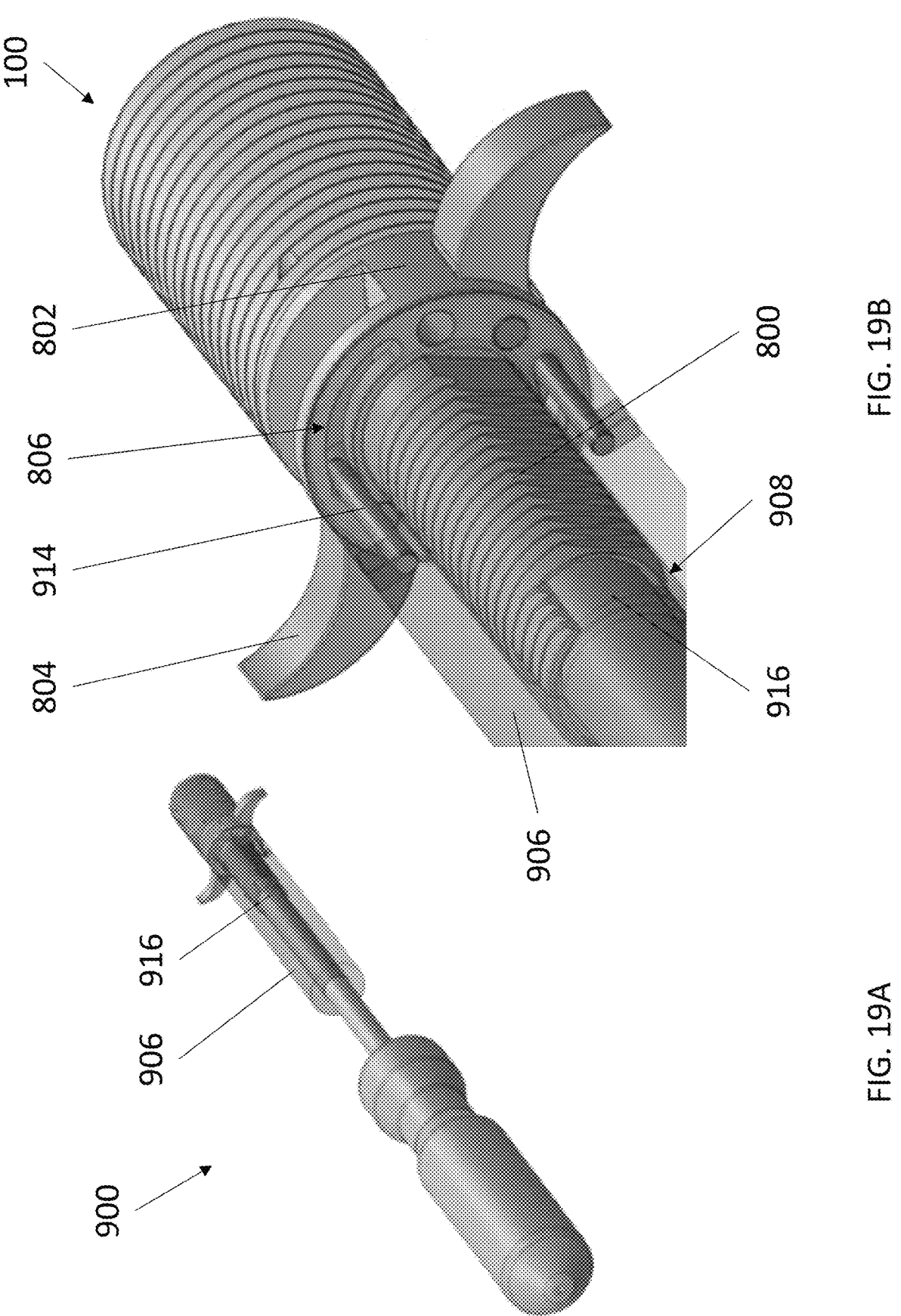
FIG. 19A and FIG. 19B depict an exemplary blade deploying tool engaged to an exemplary screw.

Blade deploying tool 900 is configured to deploy blades 804 by engaging proximal screw 800 with tongs 916 (shown in FIG. 19B) and inserting pins 914 of shaft 906 into curved slots 806 (visible in FIG. 17A). Tongs 916 are held in place to keep proximal screw 800 stationary while shaft 906 is rotated to force blades 804 away from central ring 802 (visible in FIG. 17B). In FIG. 19B, tongs 916 are rotated, wherein blades 804 catch onto surrounding material and are forced fully open to carve out the surrounding material. It should be understood that blade deploying tool 900 is secured only to proximal screw 800, such that rotating tongs 916 rotates only proximal screw 800 while the distal screw remains stationary. In some embodiments, proximal screw 800 can be actuated and deployed using screw driving tool 200 and locking tube 300, as described elsewhere herein. For example, pins 212 of screw driving tool 200 can be used similar to pins 914 of blade deploying tool 900 to fit into curved slots 806 and rotated to force blades 804 away from central ring 802. Locking tube 300 can be used similar to tongs 916 to keep proximal screw 800 stationary while screw driving tool 200 is rotated, and then to rotate proximal screw 800 to actuate proximal screw 800 and carve out material with blades 804. In various embodiments, locking tube 300 can be used interchangeably with shaft 906, and screw driving tool 200 can be used interchangeably with tongs 916.

Third Decorticating Screw

Figures 20A, 20B:
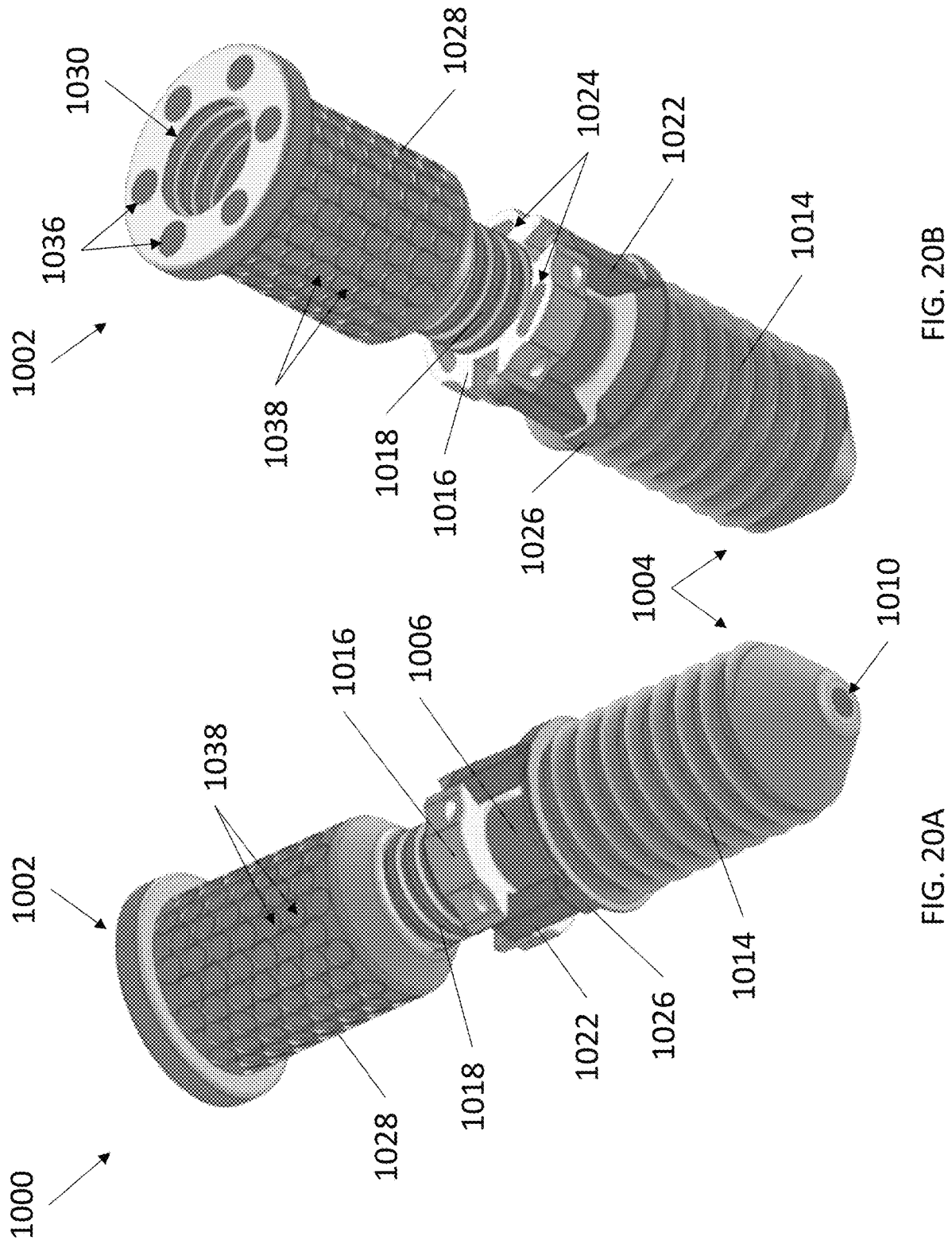
FIG. 20A and FIG. 20B depict perspective views of an exemplary screw.
Figures 21A, 21B, 21C:
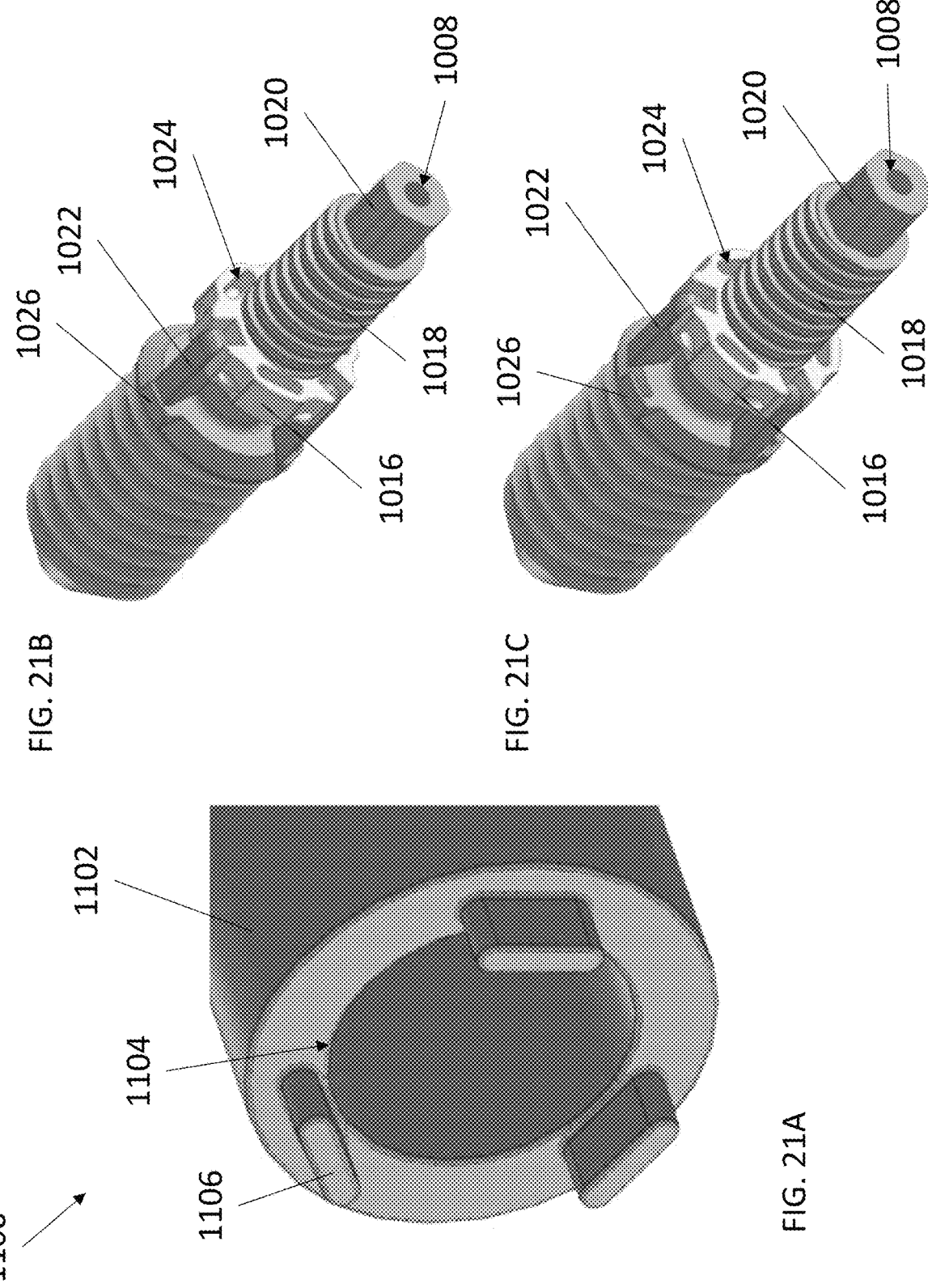
FIG. 21A through FIG. 21C depict an exemplary blade deploying tool and blade deployment in an exemplary screw.
Figure 22B:
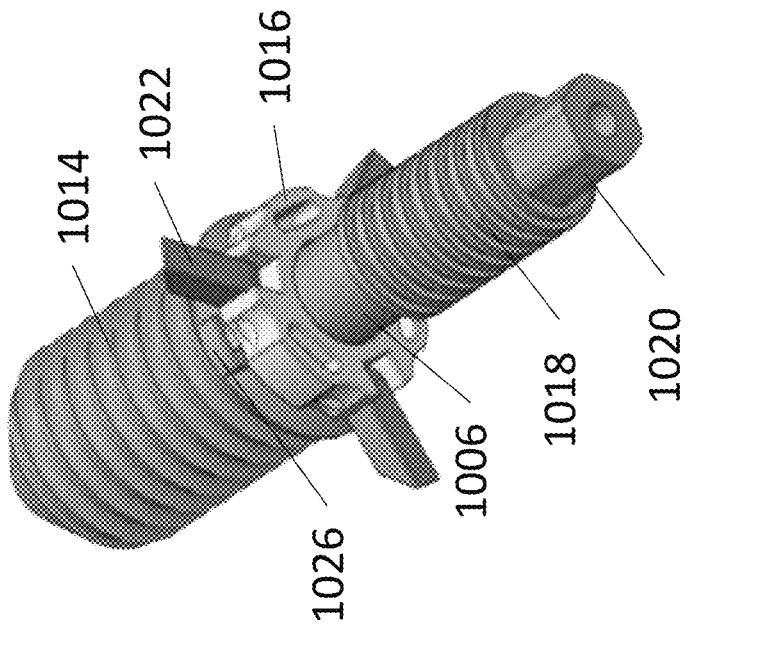
FIG. 22A and FIG. 22B depict perspective views of an exemplary screw with blades deployed.
Figure 22A:
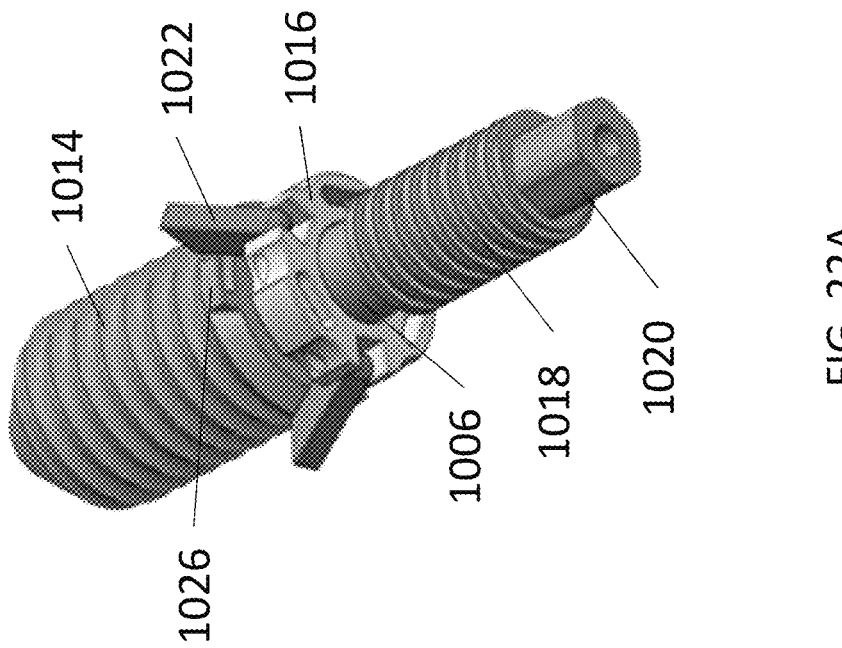
Figures 23A, 23B, 23C, 23D:
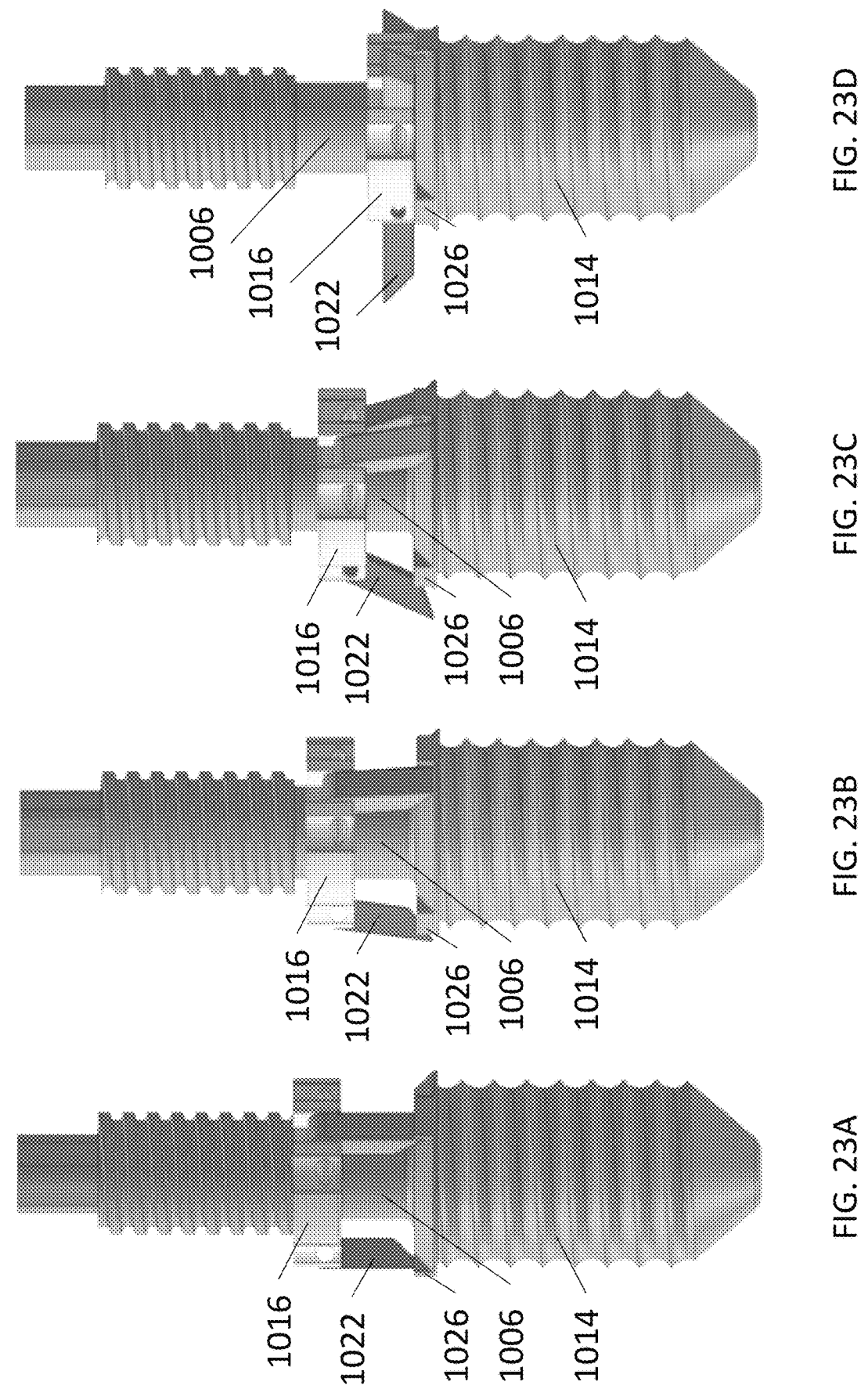
FIG. 23A through FIG. 23D depict a sequence of deploying blades in an exemplary screw.

Referring now to FIG. 20A and FIG. 20B, an exemplary screw 1000 is now described. Screw 1000 comprises a screw body 1006 having a proximal end 1002 and a distal end 1004. Screw body 1006 is a single continuous component having a lumen running between a proximal opening 1008 (visible in FIG. 21B) and a distal opening 1010. In certain embodiments, screw body 1006 comprises one or more apertures along an exterior surface that is fluidly connected to the lumen of screw body 1006 (not pictured). Screw body 1006 comprises a threaded distal section 1014 (comparable to distal screw 106 of screw 100) and a threaded proximal section 1018 (comparable to proximal stem 124 of proximal screw 118 of screw 100) having a stem bit 1020 (visible in FIG. 21B). In a central region, screw 1000 comprises a central ring 1016 (comparable to central ring 122 of screw 100). Central ring 1016 is actuatable independently from screw body 1006 and comprises one or more hinged blades 1022 and one or more tab slots 1024. The hinged connection is in perpendicular alignment with a long axis of screw 1000. Blades 1022 are held in a closed configuration by blade retainers 1026 positioned at a proximal edge of distal section 1014. Screw 1000 further comprises a cap 1028 (comparable to cap 146 of screw 100) that has a threaded lumen 1030 sized to screw onto proximal stem 1018. Cap 1028 has a proximal surface having one or more pin slots 1036, and an exterior surface that can include one or more apertures 1038 that can accept graft material or tissue ingrowth. In some embodiments, screw 1000 is compatible with cap 146 and associated cap driving tool 600 as described elsewhere herein.

Referring now to FIG. 21A through FIG. 23D, the operation of screw 1000 is now described. As described elsewhere herein, screw 1000 is similar to screw 100 in that it is provided for the locking of a first bone to a second bone. To this end, comprises three distinct regions: a first region defined by distal section 1014 that secures into a first bone; a second region defined by central ring 1016 and blades 1022 that decorticates a joint space between the first bone and a second bone; and a third region defined by proximal section 1018 and cap 1028 that secures into the second bone.

Screw 1000 can be screwed into a first bone such that distal section 1014 resides within a first bone, positioning central ring 1016 within a joint space and proximal section 1018 within a second bone. In certain embodiments, screw 1000 is driven using any suitable screw driving device having a driver tip engageable to stem bit 1020. Blades 1022 are deployed by providing a blade deploying tool 1100 having a shaft 1102 with a distal cavity 1104 sized to fit proximal section 1018 and one or more tabs 1106 sized to fit within tab slots 1024. Once blade deploying tool 1100 has been engaged to central ring 1016, a first rotation frees the tips of blades 1022 from blade retainers 1026. Central ring 1016 can then be pushed in a distal direction, causing blades 1022 to splay outwards as they run into a proximal edge of distal section 1014. Once blades 1022 are fully deployed, blade deploying tool 1100 can be actuated to carve out surrounding material using blades 1022. In some embodiments, carved away material can be removed by suction through the apertures, lumen, and proximal opening 1008 of screw 1000. Graft material can be inserted into screw 1000 by way of proximal opening 1008 (such as with graft funnel tool 500), whereupon graft material can enter the lumen of screw body 1006 and exit any one of several apertures connecting the lumen to the exterior of screw body 1006.

Figures 24A, 24B:
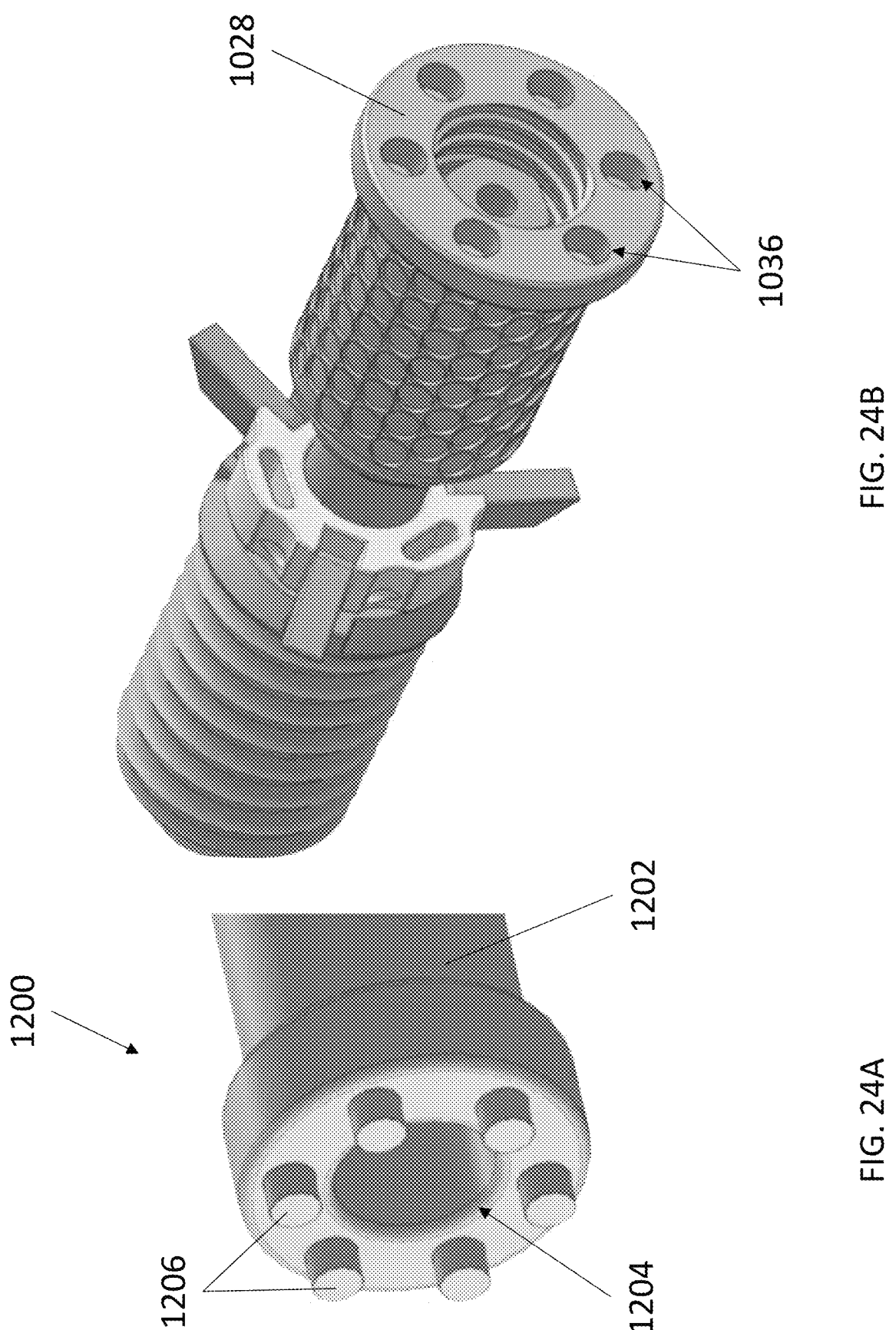
FIG. 24A and FIG. 24B depict an exemplary cap driving tool and an exemplary screw highlighting engagement points with the cap driving tool.
Figures 25A, 25B:
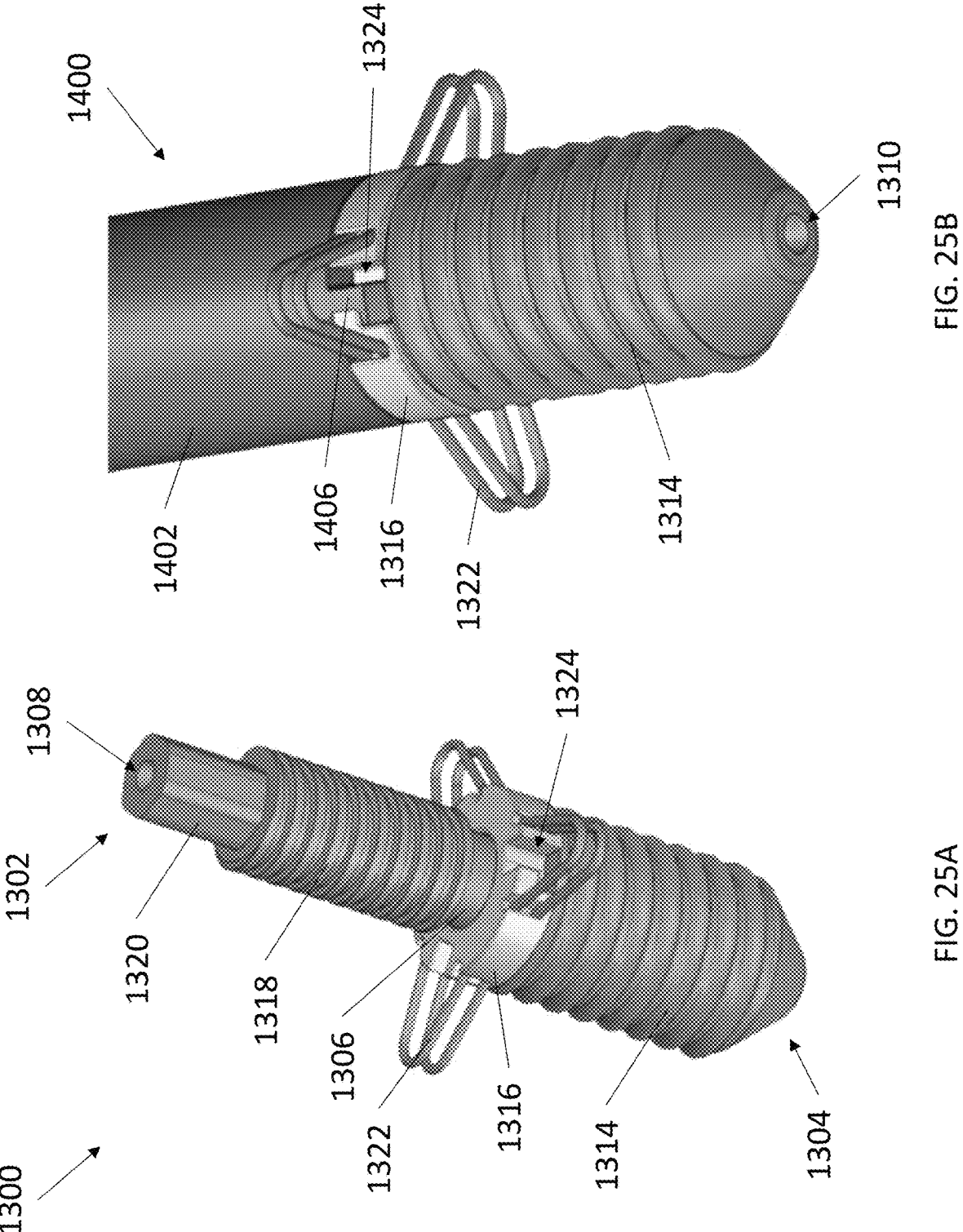
FIG. 25A and FIG. 25B depict a perspective view of an exemplary screw and the screw engaged to the distal end of an exemplary blade deploying tool.

Referring now to FIG. 24A and FIG. 24B, cap 1028 can be driven onto screw 1000 by providing a cap driving tool 1200 having a shaft 1202 with a distal cavity 1204 sized to fit proximal section 1018 and one or more pins 1206 sized to fit within pin slots 1036. Once cap driving tool 1200 is engaged to cap 1028, rotating cap driving tool 1200 screws cap 1028 onto proximal section 1018 of screw 1000.

Screw 1000 can further be compatible with any of the caps, cap driving tools, graft funnel tools, and/or lock screw drivers described elsewhere herein.

Fourth Decorticating Screw

Referring now to FIG. 25A through FIG. 26B, an exemplary screw 1300 is now described. Similar to screw 1000, screw 1300 comprises a screw body 1306 having a proximal end 1302 and a distal end 1304. Screw body 1306 is a single continuous component having a lumen running between a proximal opening 1308 and a distal opening 1310. In certain embodiments, screw body 1306 comprises one or more apertures along an exterior surface that is fluidly connected to the lumen of screw body 1306 (not pictured). Screw body 1306 comprises a threaded distal section 1314 and a threaded proximal section 1318 having a stem bit 1320. In a central region, screw 1300 comprises a central ring 1316. Central ring 1316 is actuatable independently from screw body 1306 and comprises one or more retractable wire blades 1322 and one or more tab spaces 1324 (shown in an open configuration in FIG. 25A and FIG. 25B). Wire blades 1322 are initially retracted into central ring 1316 in a closed configuration (not pictured). Screw 1300 is compatible with any of the caps and cap driving tools described elsewhere herein.

As described elsewhere herein, screw 1300 is similar to screw 1000 in that it is provided for the locking of a first bone to a second bone. To this end, screw 1300 comprises three distinct regions: a first region defined by distal section 1314 that secures into a first bone; a second region defined by proximal section 1318 and a cap that secures into a second bone; and a third region defined by central ring 1316 and wire blades 1322 that decorticates a joint space between the first bone and the second bone.

Figures 26A, 26B:
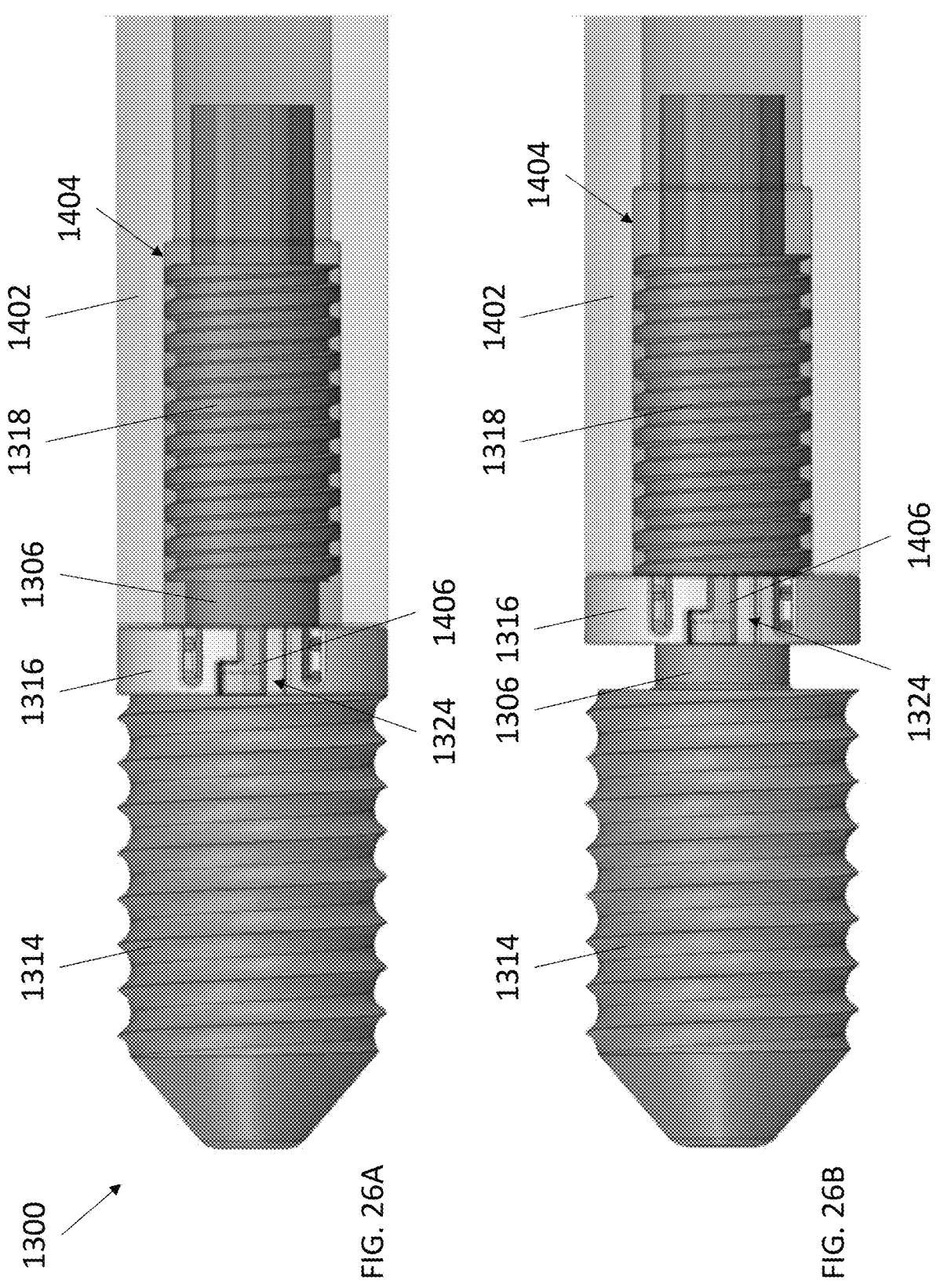
FIG. 26A and FIG. 26B depict partially transparent side views of an exemplary blade deploying tool engaged to an exemplary screw.
Figures 28A, 28B, 28C, 28D:
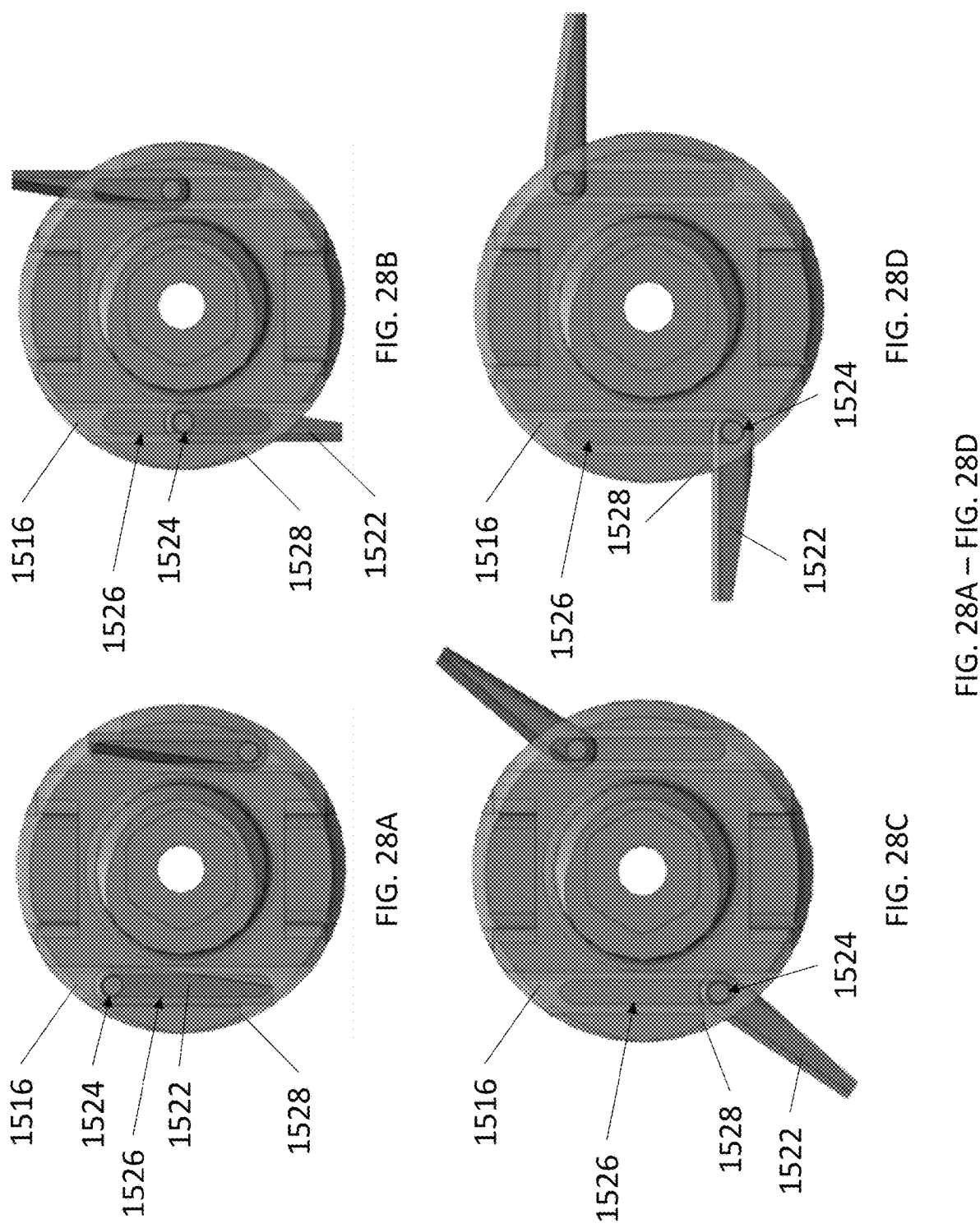
FIG. 28A through FIG. 28D depict a sequence of deploying blades in an exemplary screw. The central ring of the screw is shown partially transparent to illustrate the movement of the blades.
Figures 29A, 29B, 29C, 29D, 29E, 29F:
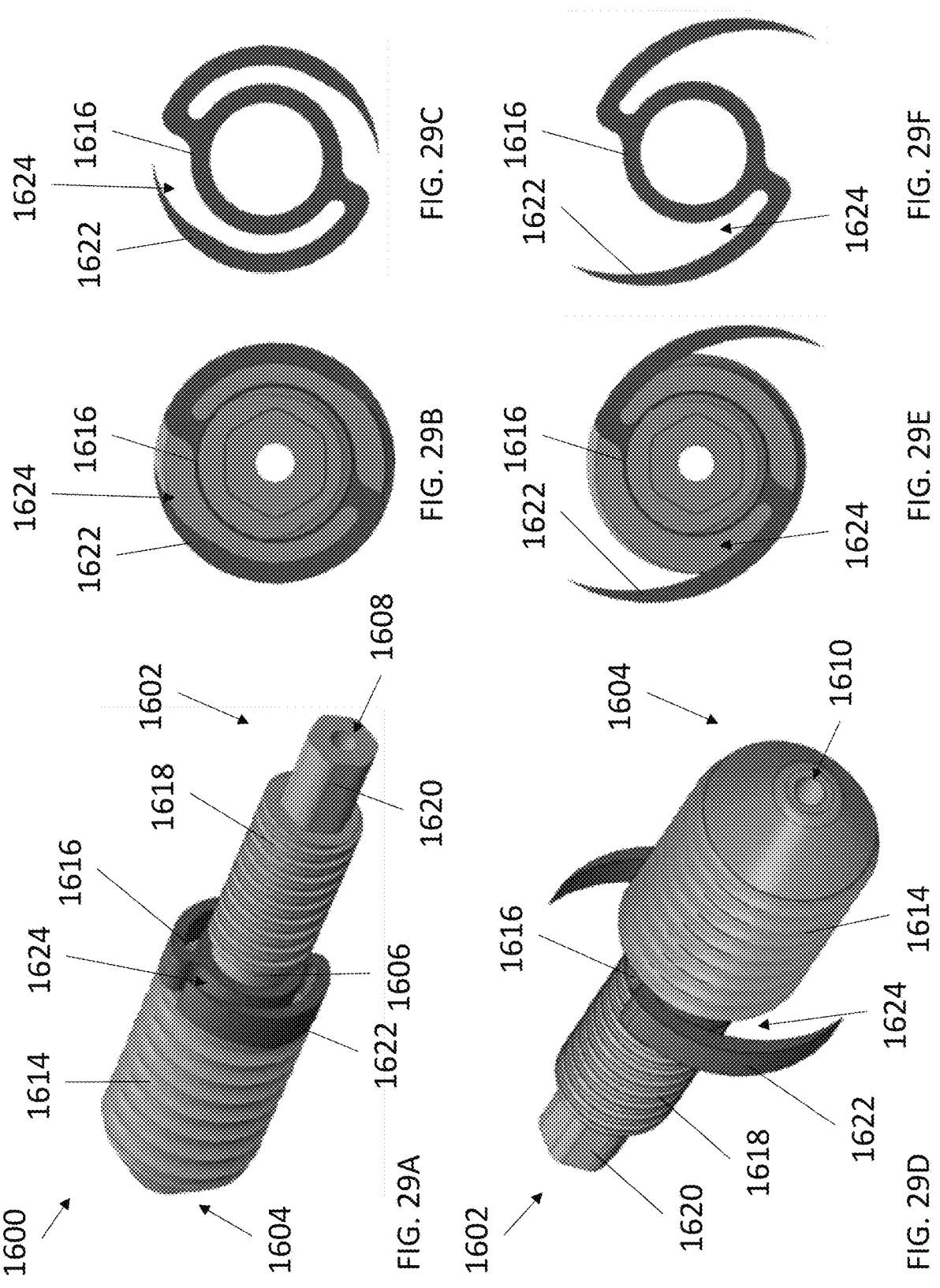
FIG. 29A through FIG. 29F depict an exemplary screw.

Screw 1300 can be screwed into a first bone such that distal section 1314 resides within a first bone, positioning central ring 1316 within a joint space and proximal section 1318 within a second bone. In certain embodiments, screw 1300 is driven using any suitable screw driving device having a driver tip engageable to stem bit 1320. Wire blades 1322 are deployed by providing a blade deploying tool 1400 having a shaft 1402 with a distal cavity 1404 sized to fit proximal section 1318 and one or more hooked tabs 1406 sized to fit within tab spaces 1324. Sliding blade deploying tool 1400 onto proximal section 1318 pushes wire blades 1322 outward from the central ring 1316 into a fully open position. Once blade deploying tool 1400 has been engaged to central ring 1316 by hooking hooked tabs 1406 into tab spaces 1324, blade deploying tool 1400 can be actuated to carve out surrounding material using wire blades 1322. Blade deploying tool 1400 can also be shifted in proximal and distal directions to carve out additional surrounding material (FIG. 26A and FIG. 26B). In some embodiments, carved away material can be removed by suction through the apertures, lumen, and proximal opening 1308 of screw 1300. Graft material can then be inserted into screw 1300 similar to methods described elsewhere herein, followed by the insertion of a cap to proximal section 1318 of screw 1300.

Fifth Decorticating Screw

Referring now to FIG. 27A through FIG. 28D, an exemplary screw 1500 is now described. Screw 1500 comprises a screw body 1506 having a proximal end 1502 and a distal end 1504. Screw body 1506 is a single continuous component having a lumen running between a proximal opening 1508 and a distal opening. In certain embodiments, screw body 1506 comprises one or more apertures along an exterior surface that is fluidly connected to the lumen of screw body 1506 (not pictured). Screw body 1506 comprises a threaded distal section 1514 (comparable to distal screw 106 of screw 100) and a threaded proximal section 1518 (comparable to proximal stem 124 of proximal screw 118 of screw 100) having a stem bit 1520. In a central region, screw 1500 comprises a central ring 1516 (comparable to central ring 122 of screw 100). Central ring 1516 is actuatable independently from screw body 1506 and comprises one or more sliding blades 1522, each positioned with a sheath and slidable along a slot 1526 by way of a pin 1524. In a closed position, blades 1522 are each fully contained within a sheath. Central ring 1516 can further comprise a blade stop 1528 adjacent to slot 1526, which is a surface that limits the swinging angle of sliding blades 1522. In some embodiments, a proximal portion of distal section 1514 and central ring 1516 each comprise an indent that are alignable to form a tong space 1530. Screw 1500 is compatible with any of the caps and cap driving tools described elsewhere herein.

As described elsewhere herein, screw 1500 is similar to screw 1000 in that it is provided for the locking of a first bone to a second bone. To this end, screw 1500 comprises three distinct regions: a first region defined by distal section 1514 that secures into a first bone; a second region defined by central ring 1516 and sliding blades 1522 that decorticates a joint space between the first bone and a second bone; and a third region defined by proximal section 1518 and a cap that secures into the second bone.

Screw 1500 can be screwed into a first bone such that distal section 1514 resides within a first bone, positioning central ring 1516 within a joint space and proximal section

1518 within a second bone. In certain embodiments, screw 1500 is driven using any suitable screw driving device having a driver tip engageable to stem bit 1520. Sliding blades 1522 are deployed by providing a blade deploying tool having a distal cavity sized to fit proximal section 1518, one or more pin holes sized to fit each pin 1524, and tongs sized to fit within tong space 1530. Once the blade deploying tool has been engaged to central ring 1516, a first rotation pushes on pins 1524 to slide blades 1522 out of their respective sheaths and into a joint space. The tongs can grip both distal section 1514 and central ring 1516 during the first rotation. Once blades 1522 have been slid out of their respective sheaths, the tongs can be moved proximally to grip and rotate only central ring 1516, wherein blades 1522 catch onto surrounding material and are forced fully open to carve out the surrounding material. Central ring 1516 can also be shifted in proximal and distal directions to carve out additional surrounding material. In some embodiments, carved away material can be removed by suction through the apertures, lumen, and proximal opening 1508 of screw 1500. Graft material can then be inserted into screw 1500 similar to methods described elsewhere herein, followed by the insertion of a cap to proximal section 1518 of screw 1500.

Sixth Decorticating Screw

Referring now to FIG. 29A through FIG. 29F, an exemplary screw 1600 is now described. Screw 1600 comprises a screw body 1606 having a proximal end 1602 and a distal end 1604. Screw body 1606 is a single continuous component having a lumen running between a proximal opening 1608 and a distal opening 1610. In certain embodiments, screw body 1606 comprises one or more apertures along an exterior surface that is fluidly connected to the lumen of screw body 1606 (not pictured). Screw body 1606 comprises a threaded distal section 1614 (comparable to distal screw 106 of screw 100) and a threaded proximal section 1618 (comparable to proximal stem 124 of proximal screw 118 of screw 100) having a stem bit 1620. In a central region, screw 1600 comprises a central ring 1616. Central ring 1616 is actuatable independently from screw body 1606 and comprises one or more bendable blades 1622. In a closed position, bendable blades 1622 are near flush against central ring 1616 with a tool space 1624 in between. Screw 1600 is compatible with any of the caps and cap driving tools described elsewhere herein.

As described elsewhere herein, screw 1600 is similar to screw 1000 in that it is provided for the locking of a first bone to a second bone. To this end, screw 1600 comprises three distinct regions: a first region defined by distal section 1614 that secures into a first bone; a second region defined by central ring 1616 and sliding blades 1622 that decorticates a joint space between the first bone and a second bone; and a third region defined by proximal section 1618 and a cap that secures into the second bone.

Screw 1600 can be screwed into a first bone such that distal section 1614 resides within a first bone, positioning central ring 1616 within a joint space and proximal section 1618 within a second bone. In certain embodiments, screw 1600 is driven using any suitable screw driving device having a driver tip engageable to stem bit 1620. Bendable blades 1622 are deployed by providing a blade deploying tool having a distal cavity sized to fit proximal section 1618 and one or more wedges sized to fit within each tool space 1624. Once the blade deploying tool has been engaged to central ring 1616, a first rotation pushes on blades 1622 to bend blades 1622 outwards and into a joint space. Once blades 1622 have been bent outwards, the blade deploying tool can be rotated in an opposing direction to rotate central ring 1616 such that blades 1622 catch onto surrounding material and are forced fully open to carve out the surrounding material. Central ring 1616 can also be shifted in proximal and distal directions to carve out additional surrounding material. In some embodiments, carved away material can be removed by suction through the apertures, lumen, and proximal opening 1608 of screw 1600. Graft material can then be inserted into screw 1600 similar to methods described elsewhere herein, followed by the insertion of a cap to proximal section 1618 of screw 1600.

The several decorticating screws and tools of the present invention described herein can be constructed from substantially rigid materials, such as a metal or a hard polymer. In some instances, components may have a degree of pliability, such as in bendable blade components. In various embodiments, the materials are biocompatible materials. In various embodiments, the decorticating screws of the present invention are compatible with any suitable graft material, including biological materials that promote the ingrowth of tissue, such as bone. Contemplated graft materials include but are not limited to autologous bone grafts, allogeneic bone grafts, xenogeneic bone grafts, hydroxyapatite, calcium phosphate, calcium sulphate, bioactive glass, polymers, cements, and the like. In some embodiments, the graft material can include a therapeutic to treat surrounding tissue. In some embodiments, one or more sensors can be inserted into the decorticating screws to monitor the device and its environs, such as a temperature sensor, pressure sensor, corrosion sensor, and the like.

The decorticating screws of the present invention can have any suitable dimensions. For example, in certain embodiments, the decorticating screws can have a length between about 10 mm to 150 mm or also between about 20 mm to 100 mm. In certain embodiments, the decorticating screws can have an outer diameter between about 5 mm to 50 mm or also between about 5 mm to 22 mm. In certain embodiments, the blades can be deployable to have an outer diameter between about 6 mm to 60 mm or also between about 6 mm to 50 mm. In certain embodiments, the decorticating screws have a threaded proximal section with a diameter that is less than a diameter of a threaded distal section. In certain embodiments, the decorticating screws have a cap with a diameter that is substantially equal to a diameter of the threaded distal section. In certain embodiments, the decorticating screws have a lock screw with a diameter larger than a diameter of the screw lumen.

Figure 30:
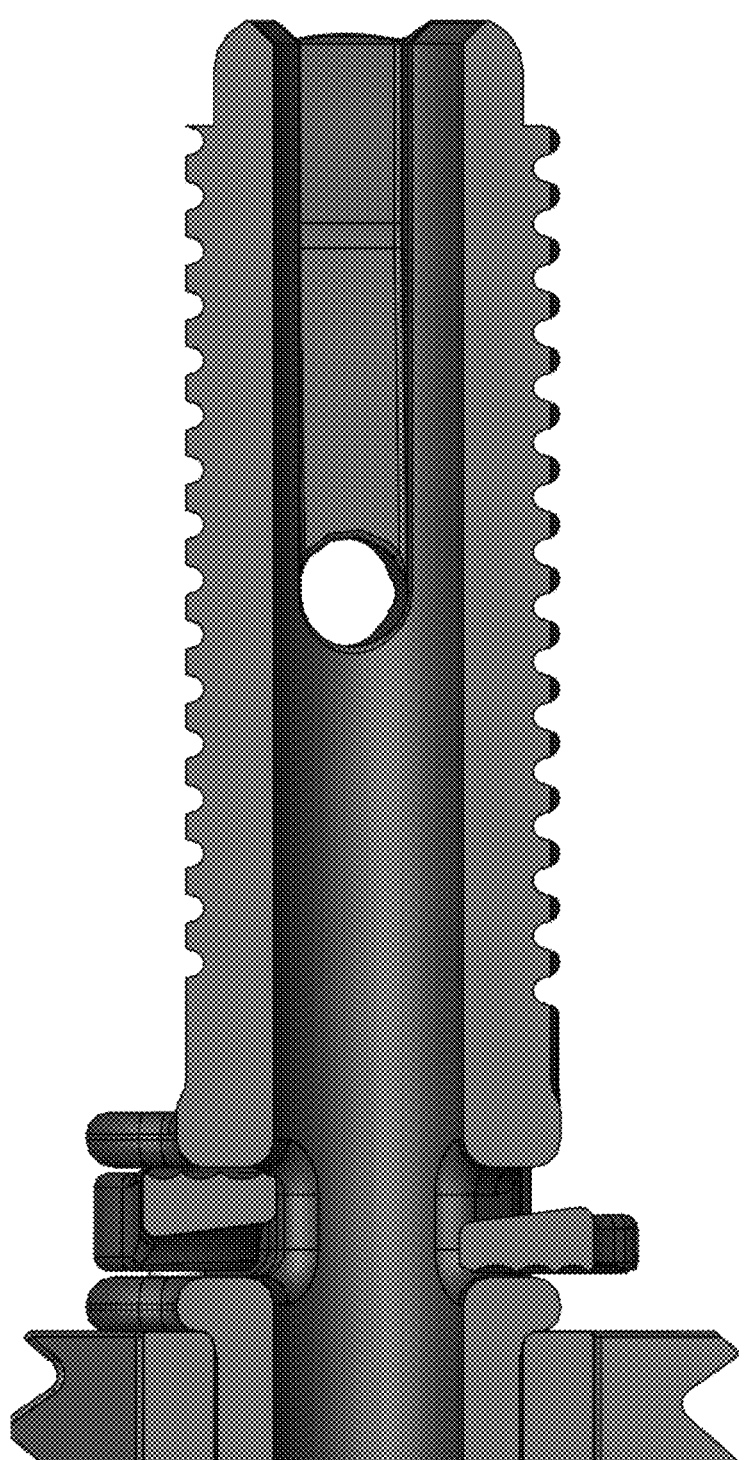
FIG. 30 depicts an exemplary decorticating screw having a proximal shaft with knuckle threading.
Figure 31:
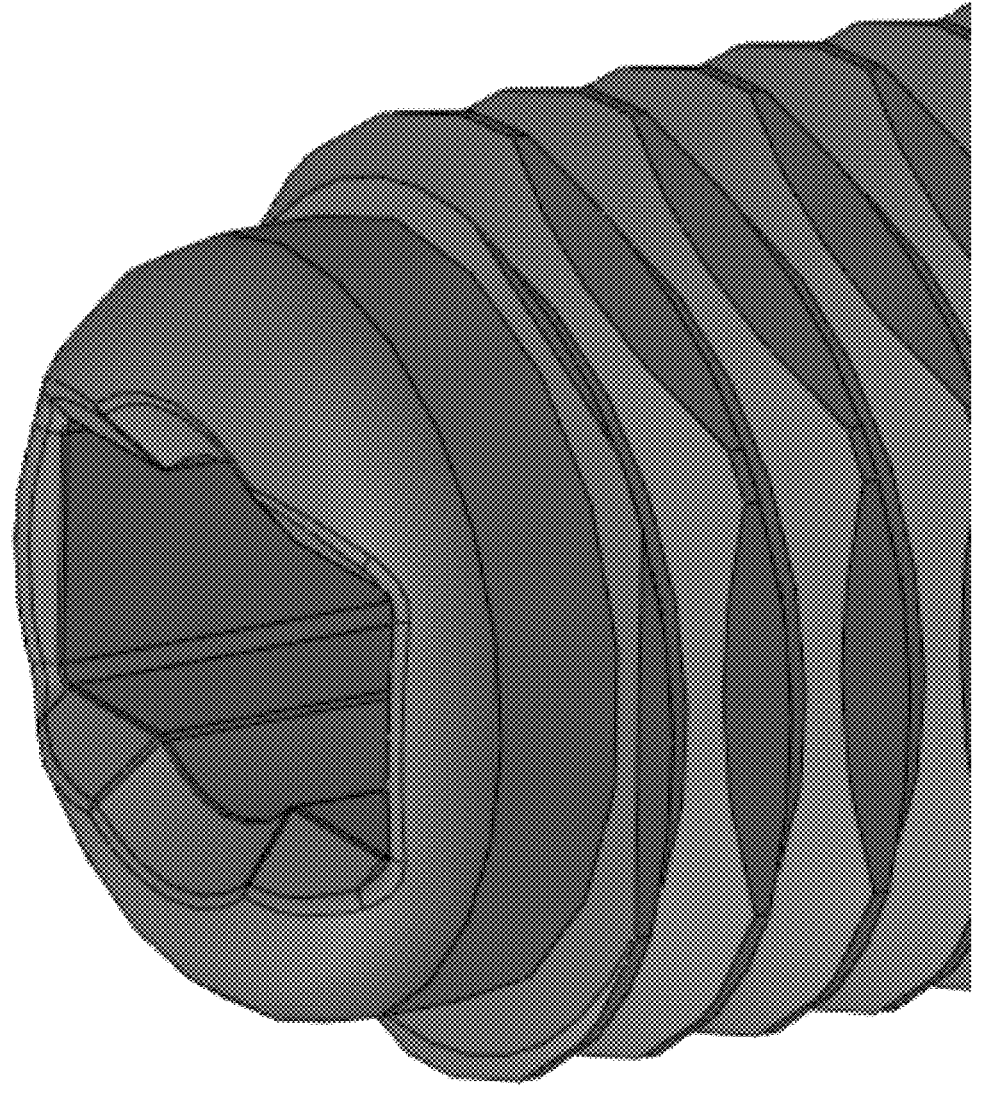
Figure 32:
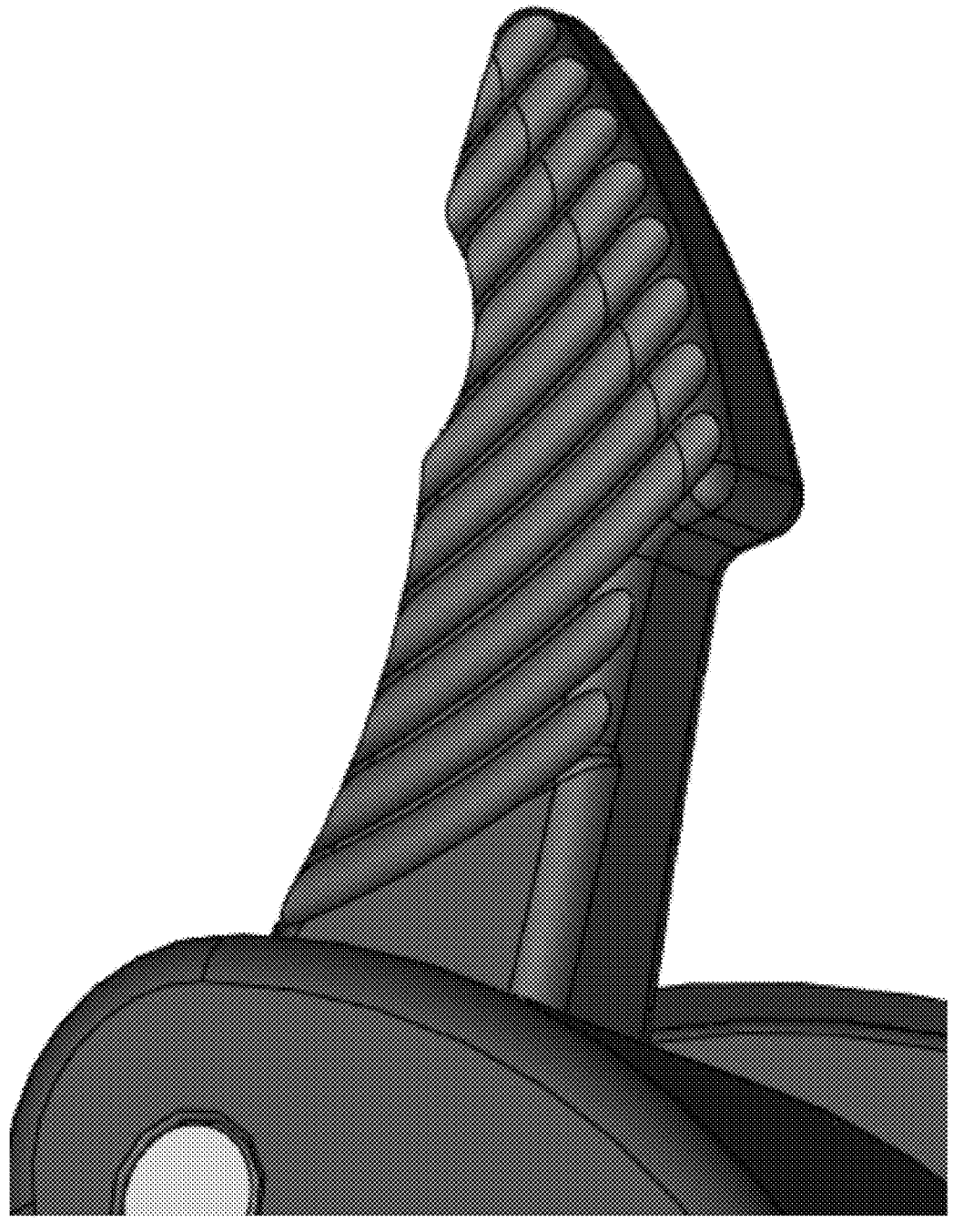
FIG. 32 depicts an exemplary decorticating screw having serrated blades.
Figure 33:
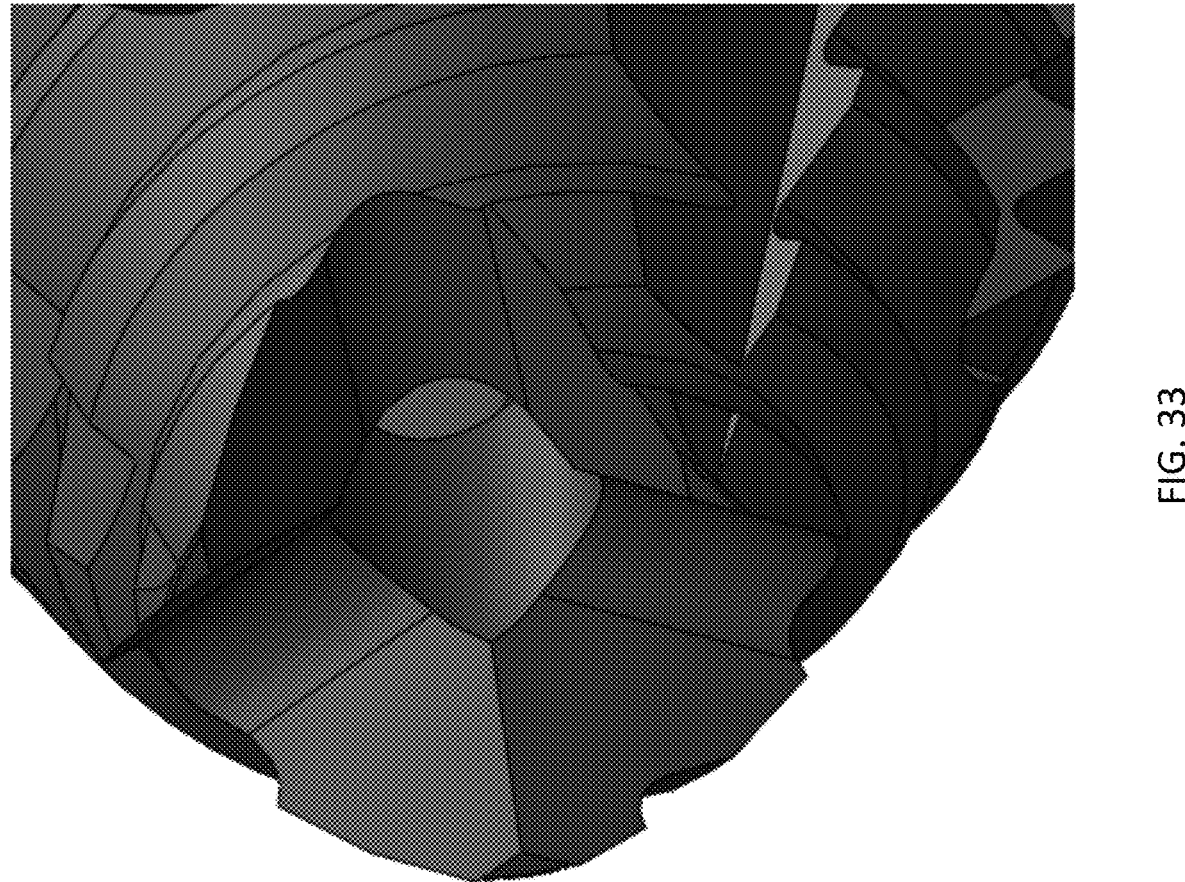
FIG. 33 depicts an exemplary decorticating screw having pointed distal tips.

The decorticating screws of the present invention are amenable to any suitable modification to enhance their function. Referring now to FIG. 30, a cross-sectional view of an exemplary proximal shaft is depicted. The proximal shaft (comparable to the proximal stems and proximal shafts described elsewhere herein) comprises an external threading having a thread form configured for enhanced cross-sectional strength, such as the depicted knuckle threading. While the depicted proximal shaft comprises a knuckle thread, it should be understood that contemplated threads include but are not limited to trapezoidal thread forms, square thread forms, buttress thread forms, and the like. Referring now to FIG. 31, the proximal end of a proximal shaft is depicted, showing a tapered or rounded proximal shaft lead in. The tapered or rounded construction of the proximal shaft lead in facilitates the engagement between the proximal shaft and a distal opening of an ilium cap (comparable to the caps configured to engage to the decorticating screws described elsewhere herein). Referring now to FIG. 32, an exemplary blade is depicted. The blade (comparable to the blades described elsewhere herein) comprises surface structures configured to enhance abrasion, such as the depicted serrations, which improves the uptake of bone graft. While the depicted blade comprises serrations, it should be understood that contemplated abrasion enhancing structures include but are not limited to embedded abrasives (such as diamond powder, aluminum oxide, silicon carbide, and the like) and micro cutting structures (such as thorns and spikes). Referring now to FIG. 33, the distal tip of an exemplary distal screw (comparable to the distal screws and distal sections described elsewhere herein) is depicted. The distal tip comprises a plurality of pointed tips that enhance decorticating screw penetration, such as with a hammer to puncture bone. In some embodiments, the pointed tips comprise external threading that is continuous with the threading of the distal screw. In other embodiments, the pointed tips do not comprise external threading. In some embodiments, the pointed tips are also self-tapping and/or self-drilling.

Figure 34:
FIG. 34 depicts an exemplary screw driving tool having dovetail-shaped pins fitting into external slots embedded in a distal screw and central ring of a decorticating screw.
Figure 35:
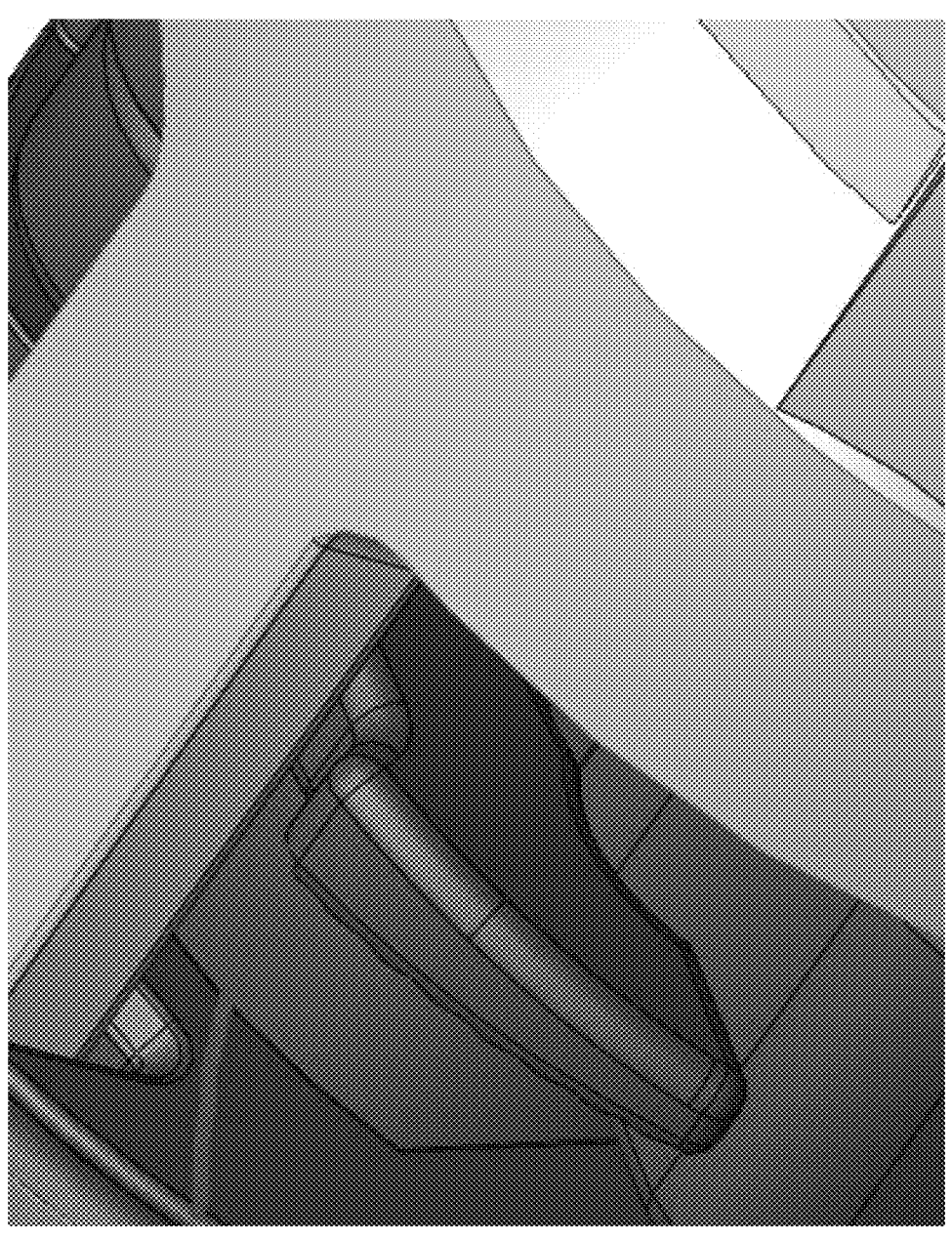
FIG. 35 depicts the exemplary screw driving tool of FIG. 34, wherein the dovetail-shaped pins slide over the blades of a decorticating screw.

Referring now to FIG. 34, the distal end of an exemplary screw driving tool is depicted. The screw driving tool (comparable to the screw driving tools described elsewhere herein) comprises dovetail-shaped pins that fit into external slots embedded in a distal screw and central ring of an exemplary decorticating screw (comparable to the decorticating screws described elsewhere herein). The dovetail shape of the pins of the screw driving tool, in combination with axial pressure applied during decorticating screw driving, prevents the screw driving tool from disengaging during operation. The dovetail-shaped pins, in fitting into external slots embedded in the distal screw and central ring, also slide over the blades of the decorticating screw (visible in FIG. 35), confining the blades in a closed position close to the body of the decorticating screw and preventing premature deployment of the blades.

Figure 36:
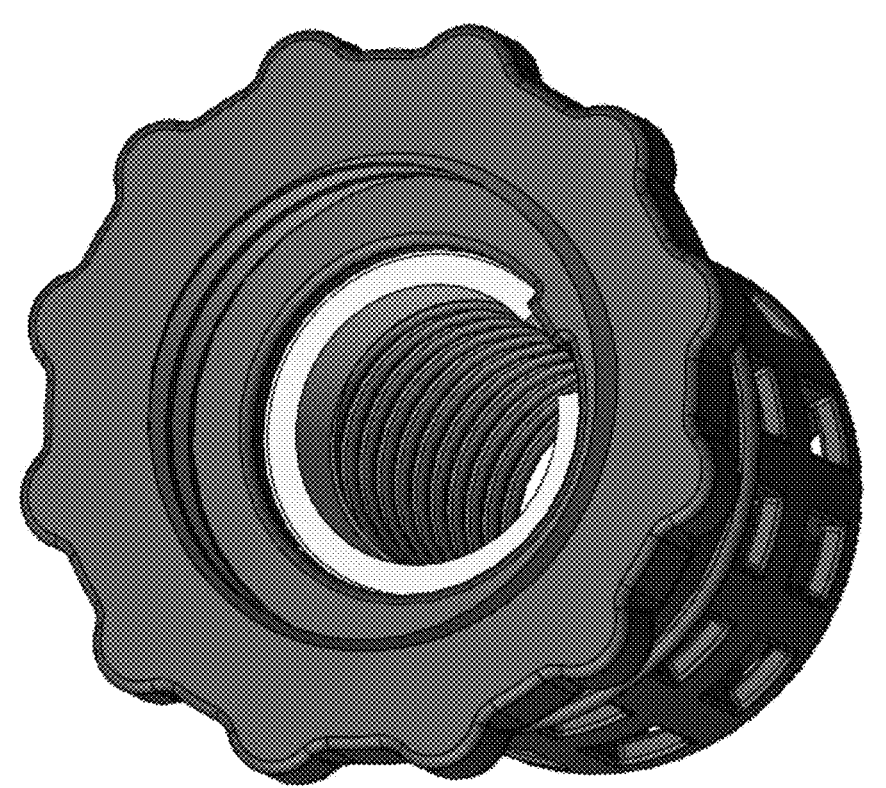
FIG. 36 depicts an exemplary cap having a thread-locking insert.
Figure 37:
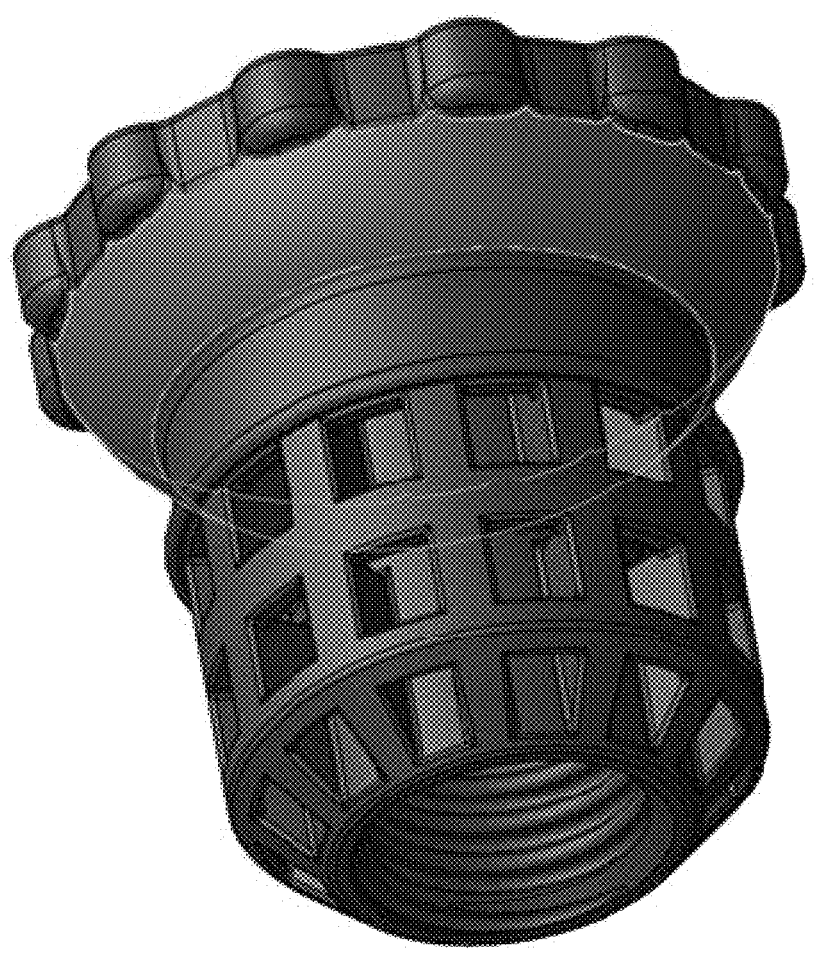
FIG. 37 depicts an exemplary cap having a convex cap lip surface.
Figure 38:
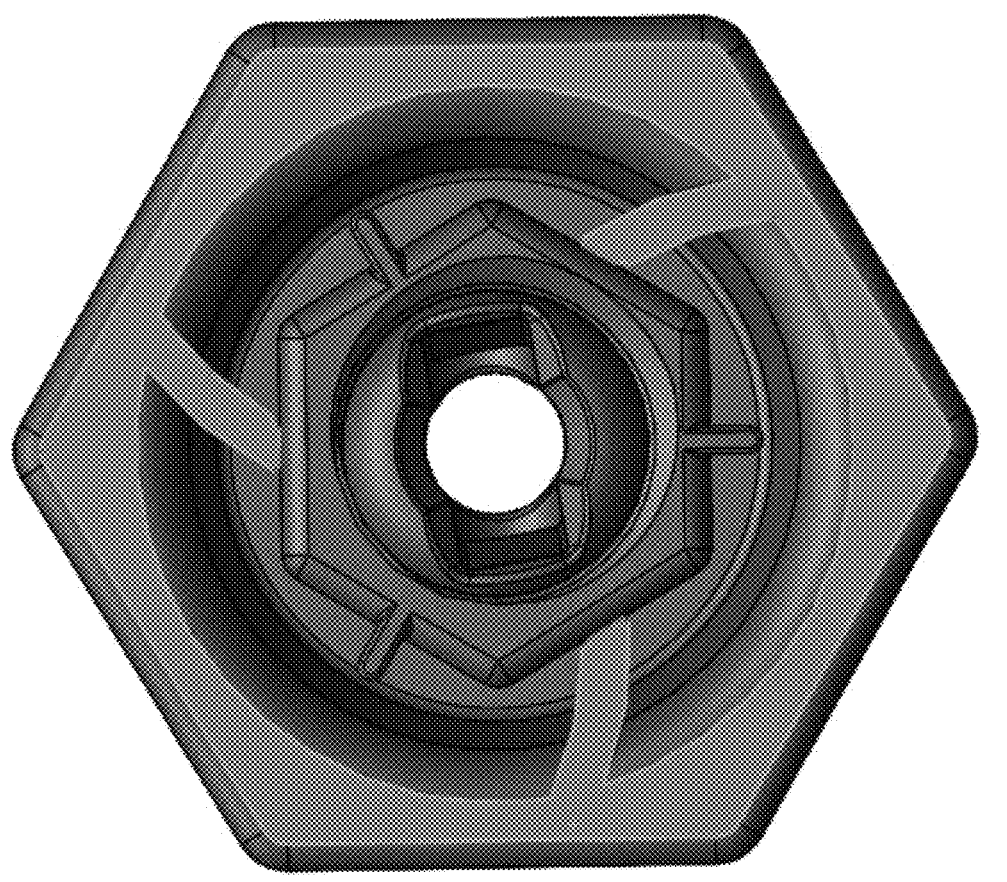
FIG. 38 depicts an exemplary cap having a locking nut.

Referring now to FIG. 36, an exemplary cap (comparable to the caps configured to engage to the decorticating screws described elsewhere herein) is depicted having a thread-locking insert positioned within its threaded lumen at a proximal end. The thread-locking insert can be constructed from any rigid material, such as ultra-high molecular weight (UHMW) polyethylene. Referring now to FIG. 37, an exemplary cap (comparable to the caps configured to engage to the decorticating screws described elsewhere herein) is depicted with a lip having a rounded distal-facing surface. The rounded distal-facing surface of the cap lip is convex in shape and improves the interface between the cap and bone surface, especially when the cap lip and the bone surface are not in parallel alignment. Referring now to FIG. 38, an exemplary cap (comparable to the caps configured to engage to the decorticating screws described elsewhere herein) is depicted partially threaded onto a proximal section of a decorticating screw, the cap having a threaded locking nut in alignment with a threaded lumen of the cap. The locking nut is fabricated with the cap as a single continuous structure, such that the locking nut is connected to the cap by one or more connecting "bridges" highlighted in FIG. 38 (three shown) as extending from a perimeter of the cap to the central hexagonal locking nut. The locking nut comprises an internal threading that is continuous with the threading of the threaded lumen, such that both the cap and the locking nut are drivable onto a proximal section of a decorticating screw. As described elsewhere herein, the cap is drivable onto a decorticating screw with a first compressive torque to compress a first bone and a second bone. After the cap is secured on the decorticating screw, the locking nut can be driven with a second locking torque that can be independent from the first compressive torque to lock the cap to the decorticating screw. The second locking torque is configured to snap or break the connecting "bridges" attaching the locking nut to the cap, such that the locking nut is independently drivable from the cap.

Figure 39:
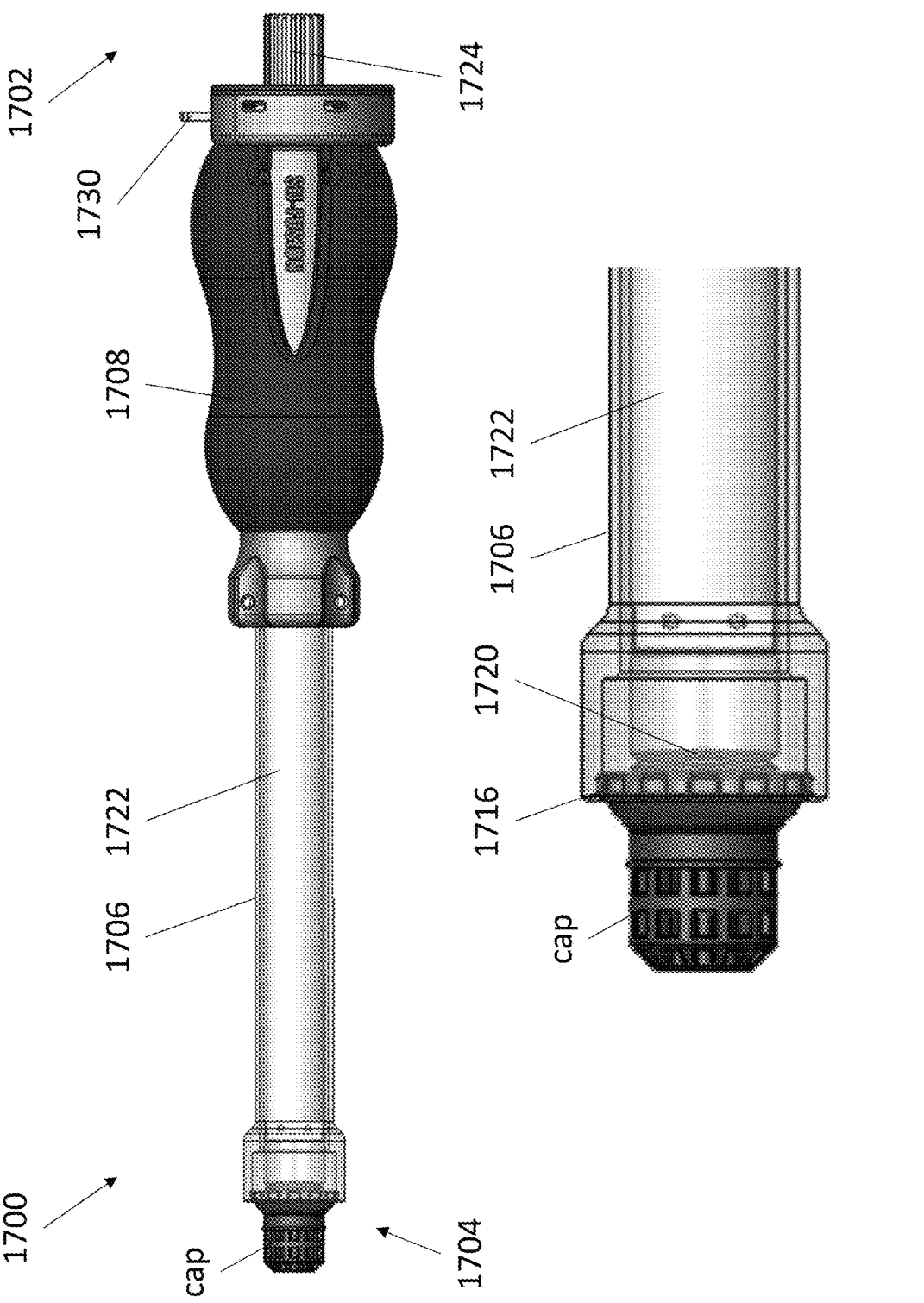
FIG. 39 depicts an exemplary cap driving tool.

Referring now to FIG. 39, an exemplary cap driving tool 1700 is depicted, tool 1700 being configured to drive a cap (comparable to the caps configured to engage to the decorticating screws described elsewhere herein). Cap driving tool 1700 has a proximal end 1702 and a distal end 1704 and comprises an outer shaft 1706 having a handle 1708, a distal cap driver 1716, and a lumen extending between a proximal opening and a distal opening. Cap driver 1716 comprises an inner geometry mated to the shape of the lip of the cap. For example, the cap depicted in FIG. 39 comprises a lip having a gear-like shape (visible in FIG. 36); accordingly, cap driver 1716 comprises an inner geometry having a complementary gear-like shape. Cap driving tool 1700 further comprises an inner shaft 1722 positioned within the lumen of outer shaft 1706, wherein inner shaft 1722 is rotatable within the lumen independently from outer shaft 1706 and comprises a retention thread 1720 at a distal end and a grip 1724 at a proximal end. Retention thread 1720 is mated to the threading of the lip of the cap. For example, the cap depicted in FIG. 39 comprises an inner threading within the lip of the cap having a wider diameter than the threaded lumen of the cap; accordingly, retention thread 1720 is threaded to mate with the inner threading of the lip of the cap. Retention thread 1720 screws into the lip of the cap to releasably secure cap driver 1716 to the proximal end of the cap. Cap driving tool 1700 further comprises button 1730 mechanically linked to a locking mechanism configured to lock or unlock rotation in inner shaft 1722 relative to outer shaft 1706. For example, in a locked configuration, inner shaft 1722 cannot rotate independently from outer shaft 1706 and cannot be removed from cap driving tool 1700, while in an unlocked configuration, inner shaft 1722 is able to rotate independently from outer shaft 1706 and can be removed from cap driving tool 1700. The locking mechanism can be any suitable mechanism, including but not limited to a ball detent lock, a friction lock, a pin lock, and the like.

Methods of Making

The decorticating screws and tools of the present invention can be made using any suitable method known in the art. The method of making may vary depending on the materials used. For example, devices substantially comprising a metal may be milled from a larger block of metal or may be cast from molten metal. Likewise, components substantially comprising a plastic or polymer may be milled from a larger block, cast, or injection molded. In some embodiments, the devices may be made using 3D printing or other additive manufacturing techniques commonly used in the art.

Methods of Use

The present invention also includes methods of using decorticating screws. As described elsewhere herein, the screws of the present invention anchor into a first bone and a second bone and include a rotatable central section that decorticates a joint space between the first bone and the second bone. In some embodiments, the screws of the present invention are useful as joint fusion devices. For example, in the case of a sacroiliac (SI) joint fusion procedure in a patient, the screws of the present invention anchor to the sacrum and the iliac bone and decorticate the SI joint. Decortication of the SI joint permits the insertion of graft material and encourages true fusion between the sacrum and iliac bone.

In a typical joint fusion procedure, a skin incision is made adjacent to a joint fusion site. The joint fusion site is identified and one or more pilot holes are drilled through the bones adjacent to the joint fusion site. Any suitable tools and techniques may be used to prepare the pilot holes. In some embodiments, the pilot holes can have a single diameter corresponding substantially to the diameter of a distal section of a screw. In some embodiments, the pilot holes can have varying diameters, such as a larger diameter in a bone corresponding to a distal section of a screw and a smaller diameter in a bone corresponding to a proximal section of a screw. The pilot holes can be smooth or tapped to have threads. Once the joint space has been prepared, one or more decorticating screws of the present invention may be used to fuse the joint.

Referring now to FIG. 40, an exemplary method 2000 of fusing a joint between a first bone and a second bone is depicted. In step 2002, a decorticating screw is provided, the screw having a threaded distal section, a threaded proximal section, a rotatable central ring having one or more blades, a lumen running between a proximal opening and a distal opening, and one or more lateral openings fluidly connected to the lumen. In step 2004, the screw is inserted into a joint in need of fixation, such that the distal section is positioned in a first bone, the proximal section is positioned in a second bone, and the central ring is positioned in a joint space between the first bone and the second bone. In step 2006, the central ring is rotated, such that the one or more blades decorticate the joint space between the first bone and the second bone. In some embodiments, decorticated material can be removed by suction through the lateral openings, lumen, and proximal opening of the screw. In step 2008, at least one graft material is packed into the proximal opening of the screw, such that the at least one graft material enters the lumen and exits the one or more lateral openings of the screw. In step 2010, a cap is placed onto the proximal section of the screw. In step 2012, a lock screw is screwed into the proximal opening of the screw.

As described elsewhere herein, the blades are deployable in different ways depending on their connection with the central ring. In one embodiment, the one or more blades are hingedly connected to the central ring along an axis that is in parallel with a long axis of the body and are laterally swung from the closed position to the open position. In one embodiment, the one or more blades are hingedly connected to the central ring along an axis that is perpendicular to a long axis of the body and splay outwards from the closed position to the open position. In one embodiment, the one or more blades are flexible wire blades retracted into the central ring in a closed position and are pushable outwards from the central ring to the open position. In one embodiment, the one or more blades are sheathed within the central ring in a closed position and are slidable outwards from the closed position to the open position. In one embodiment, the one or more blades are at least partially pliable and are bendable from a closed position to an open position.

It should be understood that the screws of the present invention are not limited to joint fusion. For example, in any various mechanical applications, there may be a need to fuse two or more solid bodies together. The screws can be used in a similar manner, wherein pilot holes are prepared across the solid bodies in need of fusion for insertion of the screws such that a distal section of the screws are positioned in a first solid body, a proximal section of the screws are positioned in a second solid body, and a bladed rotating central ring is positioned in a gap space between the first solid body and the second solid body. The central ring can be rotated to carve out material within the gap space for the insertion of glues or cements to enhance fusion between the solid bodies.

As described elsewhere herein, the screws of the present invention can be inserted with one or more sensors for monitoring performance, including temperature sensors, gyroscopes, pressure sensors, corrosion sensors, and the like.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A decorticating screw device configured for implantation in a human body, the decorticating screw device comprising:
   a substantially cylindrical body, the body having a distal threaded section, a proximal threaded section, a central ring having one or more decorticating elements;
   wherein the entire central ring is independently rotatable from the distal threaded section; and
   wherein the one or more decorticating elements are capable of maintaining a fixed position along a long axis of the cylindrical body during rotation of the central ring.

2. The device of claim 1, wherein the screw device further comprises a lumen running between a proximal opening and a distal opening.

3. The device of claim 2, wherein the screw device further comprises a cap having a threaded lumen sized to fit over the proximal threaded section of the body and a proximal lip having a diameter greater than a diameter of the cap.

4. The device of claim 3, wherein the cap comprises one or more surface voids configured to accept graft material or tissue ingrowth.

5. The device of claim 3, wherein the cap comprises a thread-locking insert positioned at a proximal end of the threaded lumen.

6. The device of claim 2, wherein the screw device further comprises one or more lateral openings fluidly connected to the lumen.

7. The device of claim 6, wherein the screw device comprises one or more cutting flutes at a distal end.

8. The device of claim 6, wherein the screw device comprises one or more pointed tips at a distal end.

9. The device of claim 6, wherein the central ring is attached to the proximal threaded section, such that the central ring and proximal threaded section are independently rotatable from the distal threaded section.

10. The device of claim 6, wherein the central ring is movable in proximal and distal directions to increase the reach of the one or more decorticating elements.

11. The device of claim 6, wherein the one or more decorticating elements are moveable between a closed position and an open position.

12. The device of claim 11, wherein the closed position positions the decorticating elements adjacent to the central ring such that they have a diameter substantially equal to a diameter of the distal threaded section, and wherein the open position positions the decorticating elements away from the central ring such that the decorticating elements extend beyond the diameter of the distal threaded section.

13. The device of claim 11, wherein the one or more decorticating elements are at least partially pliable and are bendable from a closed position to an open position.

14. The device of claim 11, wherein the one or more decorticating elements comprises at least one serration.

15. The device of claim 6, wherein the proximal threaded section has a diameter that is less than a diameter of the distal threaded section.

16. The device of claim 6, wherein the screw device has a length between about 10 mm and about 150 mm.

17. The device of claim 6, wherein the screw device has an outer diameter between about 5 mm and about 50 mm.

18. The device of claim 1, wherein at least one of the one or more decorticating elements is configured to deploy a sharpest edge furthest away from a long axis of the cylindrical body when deploying to an open position.

19. The device of claim 1, wherein the central ring is capable of maintaining a fixed position along a long axis of the cylindrical body during rotation of the central ring.

20. The device of claim 1, wherein the central ring is capable non-rotational movement along a portion of the long axis.

21. The device of claim 1, wherein the central ring is capable of maintaining a plurality of fixed positions along a long axis of the cylindrical body during rotation of the central ring.

22. The device of claim 1, wherein the one or more decorticating elements are capable of maintaining a plurality of fixed positions along a long axis of the cylindrical body during rotation of the central ring.

23. A method of fusing a joint between a first bone and a second bone, comprising the steps of:

providing a decorticating screw having a threaded distal section, a threaded proximal section, a rotatable central ring having one or more decorticating elements, a lumen running between a proximal opening and a distal opening, and one or more lateral openings fluidly connected to the lumen;

inserting the screw into a joint in need of fixation, such that the distal section is positioned in a first bone, the proximal section is positioned in a second bone, and the central ring is positioned in a joint space between the first bone and the second bone;

rotating the central ring, such that the one or more decorticating elements decorticate the joint space between the first bone and the second bone;

packing at least one graft material into the proximal opening of the screw, such that the at least one graft material enters the lumen and exits the one or more lateral openings of the screw;

placing a cap onto the proximal section of the screw; and screwing a lock screw into the proximal opening of the screw.

24. The method of claim 23, wherein the graft material is selected from the group consisting of: autologous bone grafts, allogeneic bone grafts, xenogeneic bone grafts, hydroxyapatite, calcium phosphate, calcium sulphate, bioactive glass, polymers, cements, and combinations thereof.

25. A decorticating screw device, comprising:

a substantially cylindrical body, the body having a distal threaded section, a proximal threaded section, a central ring having one or more decorticating elements;

a lumen running between a proximal opening and a distal opening of the body; and two or more external slots formed between the distal threaded section, the central ring, and the one or more decorticating elements, such that each external slot is sized to receive a pin of a screw driving device;

wherein the entire central ring is independently rotatable from the distal threaded section.

26. A decorticating screw device, comprising:

a substantially cylindrical body, the body having a distal threaded section, a proximal threaded section, a central ring having one or more decorticating elements; and a lumen running between a proximal opening and a distal opening of the body;

wherein the one or more decorticating elements are moveable between a closed position and an open position; and wherein the one or more decorticating elements are hingedly connected to the central ring along an axis that is in parallel with a long axis of the body and are laterally swung from the closed position to the open position.

27. A decorticating screw device, comprising:

a substantially cylindrical body, the body having a distal threaded section, a proximal threaded section, a central ring having one or more decorticating elements; and a lumen running between a proximal opening and a distal opening of the body;

wherein the entire central ring is independently rotatable from the distal threaded section;

wherein the one or more decorticating elements are moveable between a closed position and an open position; and wherein the one or more decorticating elements are hingedly connected to the central ring along an axis that is perpendicular to a long axis of the body and splay outwards from the closed position to the open position.

28. A decorticating screw device, comprising:

a substantially cylindrical body, the body having a distal threaded section, a proximal threaded section, a central ring having one or more decorticating elements; and a lumen running between a proximal opening and a distal opening of the body;

wherein the entire central ring is independently rotatable from the distal threaded section;

wherein the one or more decorticating elements are moveable between a closed position and an open position; and wherein the one or more decorticating elements are flexible wire blades retracted into the central ring in a closed position and are pushable outwards from the central ring to the open position.

29. A decorticating screw device, comprising:

a substantially cylindrical body, the body having a distal threaded section, a proximal threaded section, a central ring having one or more decorticating elements; and a lumen running between a proximal opening and a distal opening of the body;

wherein the entire central ring is independently rotatable from the distal threaded section;

wherein the one or more decorticating elements are moveable between a closed position and an open position; and wherein the one or more decorticating elements are sheathed within the central ring in a closed position and are slidable outwards from the closed position to the open position.

30. A decorticating screw device, comprising:

a substantially cylindrical body, the body having a distal threaded section, a proximal threaded section, a central ring having one or more decorticating elements;

a lumen running between a proximal opening and a distal opening of the body; and a lock screw having a diameter larger than a diameter of the screw device lumen, the lock screw being drivable into the proximal opening of the screw device to expand a proximal end of the screw device;

wherein the entire central ring is independently rotatable from the distal threaded section.

31. A decorticating screw device configured for implantation in a human body, the decorticating screw device comprising:

a substantially cylindrical body, the body having a distal threaded section, a proximal threaded section, a central ring having one or more decorticating elements;

wherein the entire central ring is independently rotatable from the distal threaded section; and wherein the screw device further comprises a lumen running between a proximal opening and a distal opening, the proximal opening and the distal opening lying along a central longitudinal axis of the substantially cylindrical body.

32. A decorticating screw device configured for implantation in a human body, the decorticating screw device comprising:

a substantially cylindrical body, the body having a distal threaded section, a proximal threaded section, a central ring having one or more decorticating elements;

wherein the entire central ring is independently rotatable from the distal threaded section; and wherein at least one of the one or more decorticating elements is configured to deploy a sharpest edge furthest away from a long axis of the cylindrical body when deploying to an open position.

33. A decorticating screw device configured for implantation in a human body, the decorticating screw device comprising:

a substantially cylindrical body, the body having a distal threaded section, a proximal threaded section, a central ring having one or more decorticating elements;

wherein the entire central ring is independently rotatable from the distal threaded section; and wherein the central ring is capable of non-rotational movement along a portion of a long axis of the cylindrical body.

* * * * *